United States Patent
Gustafson et al.

(10) Patent No.: US 12,312,354 B2
(45) Date of Patent: May 27, 2025

(54) SELECTIVE BTK IRREVERSIBLE INHIBITORS

(71) Applicant: SAN DIEGO STATE UNIVERSITY FOUNDATION, San Diego, CA (US)

(72) Inventors: Jeffrey L. Gustafson, San Diego, CA (US); Sean Thomas Toenjes, San Diego, CA (US); Samuel T. Albright, San Diego, CA (US); Ramsey Hazin, San Diego, CA (US)

(73) Assignee: SAN DIEGO STATE UNIVERSITY (SDSU) FOUNDATION, San Diego, CA (US)

( * ) Notice: Subject to any disclaimer, the term of this patent is extended or adjusted under 35 U.S.C. 154(b) by 776 days.

(21) Appl. No.: 17/619,688

(22) PCT Filed: Jun. 23, 2020

(86) PCT No.: PCT/US2020/039132
§ 371 (c)(1),
(2) Date: Dec. 16, 2021

(87) PCT Pub. No.: WO2020/263822
PCT Pub. Date: Dec. 30, 2020

(65) Prior Publication Data
US 2022/0306638 A1 Sep. 29, 2022

Related U.S. Application Data

(60) Provisional application No. 62/866,507, filed on Jun. 25, 2019.

(51) Int. Cl.
*C07D 487/04* (2006.01)
*A61P 35/00* (2006.01)

(52) U.S. Cl.
CPC ............ *C07D 487/04* (2013.01); *A61P 35/00* (2018.01)

(58) Field of Classification Search
CPC .............................. C07D 487/04; A61P 35/00
See application file for complete search history.

(56) References Cited

U.S. PATENT DOCUMENTS

| 2015/0239900 A1 | 8/2015 | Li et al. |
| 2017/0224819 A1 | 8/2017 | Hamdy et al. |

FOREIGN PATENT DOCUMENTS

| WO | 2012158764 A1 | 11/2012 |
| WO | 2013191965 A1 | 12/2013 |

(Continued)

OTHER PUBLICATIONS

International Search Report & Written Opinion mailed, Oct. 26, 2020 for corresponding International Application No. PCT/US2020/039132.

(Continued)

*Primary Examiner* — James H Alstrum-Acevedo
*Assistant Examiner* — Justin Christopher Sanchez
(74) *Attorney, Agent, or Firm* — Haukaas Fortius PLLC; Michael Haukaas

(57) ABSTRACT

The invention provides a series of conformationally stable and selective, irreversible kinase inhibitors, and methods of using the kinase inhibitors. The effect of atropisomerism on kinase selectivity was assessed, finding improved selectivity compared to rapidly interconverting parent compounds. The compounds herein are atropisomers having increased kinase selectivity and are for use in treating conditions that benefit from selective BTK kinase inhibition.

18 Claims, 6 Drawing Sheets

(56) References Cited

FOREIGN PATENT DOCUMENTS

| WO | 2014022569 A1 | 2/2014 | | |
|---|---|---|---|---|
| WO | 2014078578 A1 | 5/2014 | | |
| WO | WO-2014188173 A1 * | 11/2014 | ........... | C07D 487/04 |
| WO | 2017046739 A1 | 3/2017 | | |

OTHER PUBLICATIONS

International Preliminary Report on Patentability, mailed Jan. 6, 2022 for corresponding International Application No. PCT/US2020/039132.

* cited by examiner

SELECTIVE BTK IRREVERSIBLE INHIBITORS

RELATED APPLICATIONS

This application is a National Stage filing under 35 U.S.C. § 371 of International Application No. PCT/US2020/039132, filed Jun. 23, 2020, which claims priority under 35 U.S.C. § 119 (e) to U.S. Provisional Patent Application No. 62/866,507 filed Jun. 25, 2019, which applications are incorporated herein by reference.

GOVERNMENT SUPPORT

This invention was made with government support under Grant No. 1R35 GM124637 awarded by the National Institutes of Health. The government has certain rights in the invention.

BACKGROUND OF THE INVENTION

The human genome contains over 500 protein kinases. These kinases affect intracellular signal transduction pathways through protein phosphorylation. Aberrant kinase activity has been implicated in numerous diseases, leading to an intense drug discovery effort to develop efficacious anti-kinase therapeutics, resulting in over 20 FDA approved targeted kinase inhibitors mainly for the treatment of cancers including chronic myeloid leukemia and non-small cell lung cancer. While these efforts have revolutionized cancer therapy, a large degree of active site conservation throughout the kinase family causes most kinase inhibitors to possess promiscuous inhibition activities towards many kinases. While often needed for a complete response, this polypharmacology can also lead to side effects that negatively affect the quality of life, largely preventing kinase inhibitors from becoming therapeutics for chronic non-lethal diseases such as rheumatoid arthritis, where selectivity becomes a much larger requirement.

Burton's Tyrosine Kinase (BTK) is a nonreceptor tyrosine kinase involved in the B-cell receptor (BCR) signaling pathway. After stimulation from an antigen, BCR activates Syk which then induces BTK phosphorylation and activation. Constitutive activation of BCR signaling leads to types of non-hodgkins lymphoma and leukemias. Because BTK has a well-defined ATP active site and is downstream of BCR, BTK has become an attractive therapeutic target to attenuate the BCR signaling pathway for the treatment of various B-cell malignancies. This has led to development of two FDA approved BTK inhibitor drugs, Ibrutinib (2013) and Acalabrutinib (2017) for mantle cell lymphoma (MCL) and chronic lymphocytic leukemia (CLL). Both of these inhibitors, along with many other BTK inhibitors, covalently target BTK's Cys481 residue found in the ATP phosphate binding pocket via an electrophilic motif (i.e. acrylamide). While these inhibitors possess high affinity towards their target, most also potently inhibit off-target kinases with particular biases towards kinases that contain a cysteine residue in a similar region as BTK such as EGFR, ITK, and TEC. Off-target inhibition of these kinases in patients are attributed to adverse events including arthralgias, atrial fibrillation and major hemorrhage. New BTK inhibitor therapies have focused on increasing the selectivity for BTK.

Recently, BTK has been shown to be involved in the excessive immune response to severe acute respiratory syndrome coronavirus 2 (SARS-CoV-2) causing a respiratory illness known as coronavirus disease 2019 (COVID-19). The later, more severe, stages of COVID-19 are believed to be associated with a virus-induced hyperinflammatory response, activating other immune cells, including macrophages and neutrophils, through a large efflux of messenger proteins called cytokines. Macrophage's production of cytokines occurs when Toll-like receptors bind the virus's RNA and activate regulatory transcription factors such as NF-kB and IFN. BTK and HCK, among other proteins, have been identified in TLR-mediated signaling, predominantly through the ERK1/2 pathway. In preliminary clinical studies, treatment of severe COVID-19 patients that are on supplemental oxygen or mechanical ventilation with a BTK inhibitor, has improved their oxygenation, discharge rate and survival rate. BTK inhibitors represent a potential therapy for the older and immune-compromised COVID-19 patients.

Kinase inhibitors are also common chemical probes to elucidate the role of a kinase or signaling pathways in cellular processes or disease. These fundamental studies are frequently confounded by off-target kinase inhibition affecting unintended signaling pathways. In recent years chemists and biologists have begun to gain an understanding of factors that can contribute to increasing the selectivity of a small molecule towards a specific kinase using 'selectivity filters' that take advantage of unusual features in a kinase active site, to obtain highly selective kinase inhibitors. A general selectivity filter has remained elusive as by design they rely on rare occurrences in an active site. Accordingly, a selectivity filter in kinase inhibition is needed in the art.

Atropisomerism is a form of chirality that arises from hindered rotation around an axis that renders the rotational isomers enantiomers. Many biologically active small molecules possess little hindrance to rotation and exist as a rapidly interconverting mixture of atropisomers yet bind to their respective biological targets in an atropisomer specific manner. This dynamic nature of atropisomerism can cause serious complications in drug development, as atropisomers can display drastically different pharmacological profiles. This often results in confounding effects caused by the non-target relevant atropisomer, particularly when a compound possesses an intermediate stability, and can racemize over the length of the experiment.

Researchers have synthesized atropisomerically stable analogs of a lead molecule and have observed striking differential target affinities between the separated atropisomers (Zask et al., *Chirality* 2013, 25, 265-274; Porter et al., *Bioorg. Med. Chem. Lett.* 2009, 19, 1767-72), including a seminal report with a p38 MAP kinase inhibitor (Xing et al., *ChemMedChem* 2012, 7, 273-280). Atropisomerically pure analogs can also possess an improved toxicological profile since the non-target binding atropisomer is precluded. For example, Yoshida has recently synthesized atropisomeric lamellarin analogs, and found that each atropisomer possesses a notably different kinase inhibition profile with one atropisomer possessing improved selectivity compared to the parent molecule (Yoshida et al., *J. Med. Chem.* 2013, 56, 7289-7301). Accordingly, new atropisomers and methods for their preparation and evaluation are needed to provide improved kinase inhibitors with enhanced selectivity for scientific and medical applications.

SUMMARY

This invention uses conformational control of BTK inhibitors' atropisomeric axis and chair orientation to increase the selectivity towards BTK. Through the addition of various conformational controlling groups ortho to the atropisomeric axis, the described inhibitors have unique low energy conformations about the axis that bind favorably to BTK. These inhibitors' axial chirality span the gamut of stereochemical stability, existing either as enantiopure stable atropisomers with half-life to racemization on the year time scale or rapidly interconverting between atropisomers in seconds. Regardless of the inhibitor's stereochemical stability, these inhibitor's substituents are selected to constrain the inhibitor to a conformation preferred by BTK and not off-target kinases (FIG. 1). This strategy has then been applied to the piperidine or pyrrolidine conformations which directs the inhibitor's electrophile to BTK's nucleophilic Cys481 (FIG. 2).

Accordingly, this disclosure provides an atropisomer compound of Formula I:

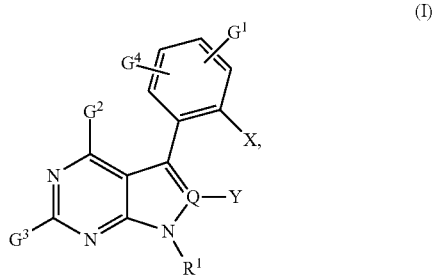

(I)

or salt thereof;
wherein
  $G^1$ is aryloxy, halo, hydroxy, alkyl, alkoxy, amino, amido, or phenyl;
  $G^2$ is amino, halo, hydroxy, alkyl, alkoxy, aryloxy, amido, or phenyl;
  $G^3$ and $G^4$ are independently H, halo, hydroxy, alkyl, alkoxy, or amino;
  Q is C or N;
  X and Y taken together form an atropisomerism rotational blocking moiety; and
  $R^1$ is a buttressing substituent wherein the buttressing substituent comprises a ring heteroatom and an electrophile;
wherein the atropisomer is atropisomerically stable; and
wherein the selectivity of the atropisomer is modulated compared to a corresponding rapidly interconverting parent kinase inhibitor, wherein the atropisomerism rotational blocking moiety of the atropisomer in combination with the buttressing substituent produces a barrier to rotation of at least 10 kcal/mol, and the atropisomeric purity of the atropisomer has a half-life of at least 8 hours, thereby stabilizing atropisomerism of the atropisomer having modulated kinase selectivity.

Additionally, this disclosure provides a method of inhibiting the growth of cancer cells comprising contacting cancer cells with an effective amount of an atropisomer disclosed above, thereby inhibiting the growth of the cancer cells.

The disclosure also provides a therapeutic method of treating hyperinflammatory diseases comprising administering to a mammal having an immune-involved response an effective amount of a compound or composition described herein.

The invention additionally provides novel compounds of Formulas I-V, IB and IIB, intermediates for the synthesis of the compounds of Formulas I-V, IB and IIB, as well as methods of preparing the compounds of Formulas I-V, IB and IIB. The invention further provides compounds of Formulas I-V, IB and IIB that are useful as intermediates for the synthesis of other useful compounds. The invention provides for the use of compounds of Formulas I-V, IB and IIB for the manufacture of medicaments useful for the treatment of conditions that can be treated by kinase inhibitors.

Thus, the invention provides for the use of the compounds and compositions described herein for medical therapy. The medical therapy can be treating cancer, for example, breast cancer, lung cancer, such as non-small cell lung cancer, pancreatic cancer, prostate cancer, colon cancer, chronic myeloid leukemia, or thyroid cancer. The medical therapy can also be used to treat COVID-19 patients with severe respiratory illness and other autoimmune disorders leading to hyper inflammatory response, for example rheumatoid arthritis and novel viral infections in the future. The invention also provides for the use of a composition as described herein for the manufacture of a medicament to treat a disease in a subject, for example, cancer or COVID-19 in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
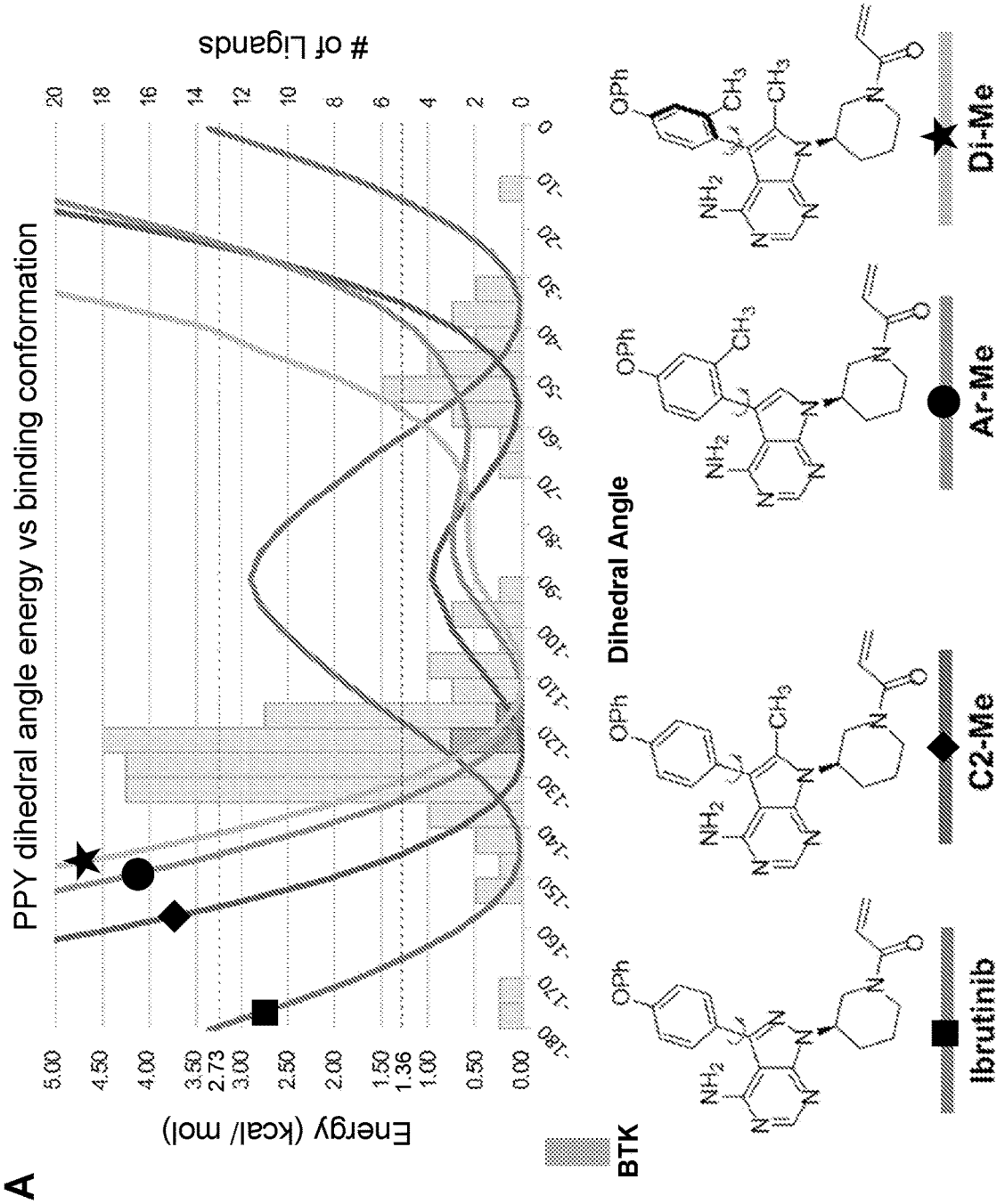
FIG. 1. (A) Conformational Energy plots. Analysis of conformational energy profiles for certain scaffolds superimposed with the dihedral angles of co-crystalized PPY ligands obtained from Protein Data Bank (PDB). BTK co-crystallized ligand dihedral angles are labeled in pink. (B) PDB structural analysis of PP or PPY ligands superimposed with CEP's of Ibrutinib and conformationally-tuned series of BTK inhibitors.
Figure 1:
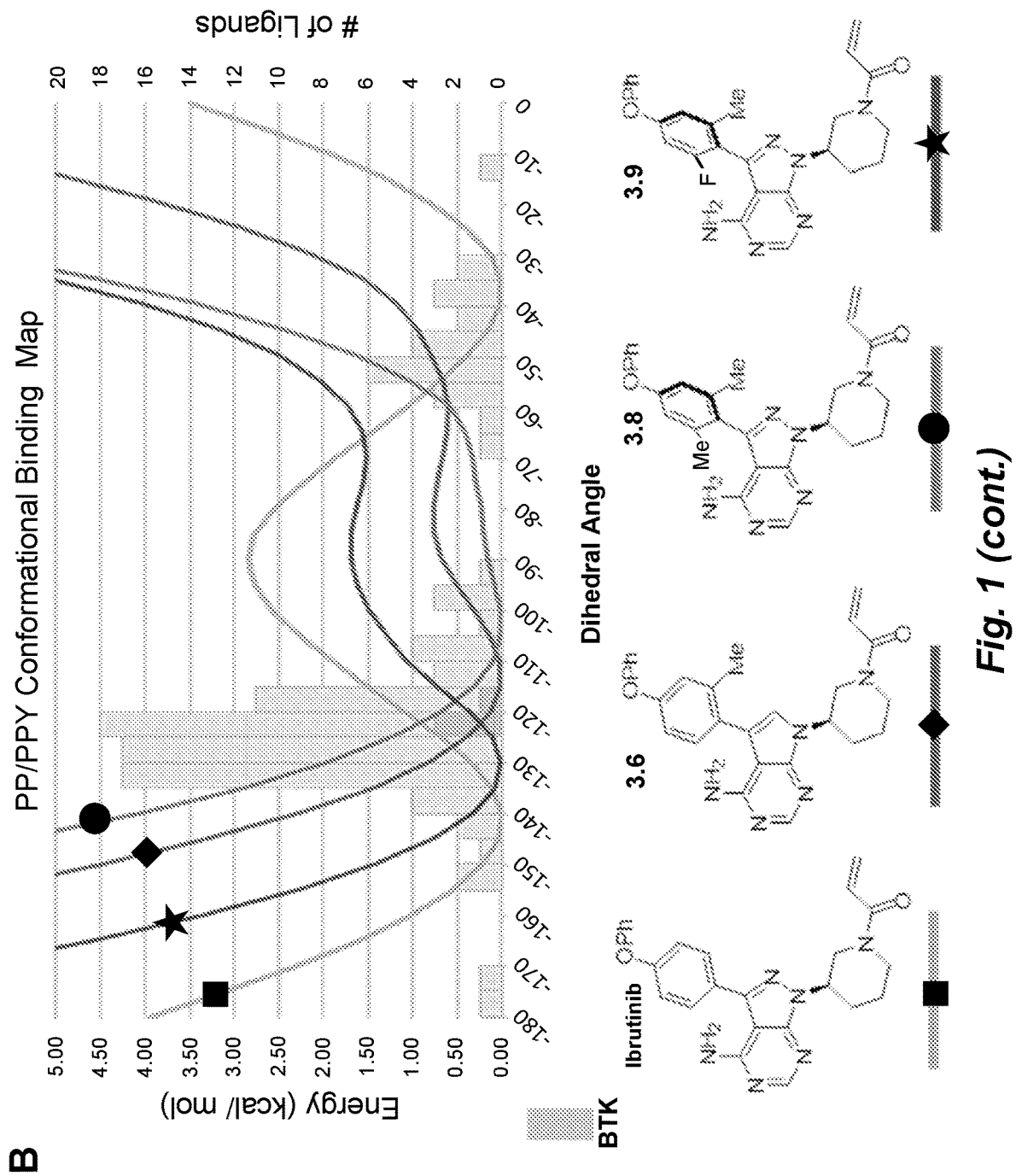

Atropisomerism is a type of dynamic axial chirality that exists about a differentially substituted $sp^2$-$sp^2$ bond. Simple bond rotation allows access to each enantiomer or atropisomer, however depending on the size of substituents adjacent to the atropisomeric axis, the molecule can exist as a racemizing mixture or stable, separable atropisomers. 83% of FDA approved kinase inhibitors, including Ibrutinib and Acalabrutinib, possess an atropisomeric axis. While these inhibitors are considered achiral, they bind their biological target in a specific conformation, with one atropisomer contributing to majority of the desired effects.

Many biologically active molecules exist as rapidly interconverting atropisomeric mixtures. While one atropisomer inhibits the desired target, the other can lead to off-target effects. Herein atropisomerism is analyzed as a tool to improve the selectivities of kinase inhibitors via the synthesis of conformationally stable pyrrolopyrimidines. Different selectivity patterns between atropisomers were observed, as well as improved selectivity compared to a rapidly interconverting parent molecule.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The term "about" can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, composition, or embodiment. The term about can also modify the end-points of a recited range as discussed above in this paragraph.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2, 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups when specifically noted. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 or from 3 to 8 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" or "heterocyclyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 20 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "halo" or "halide" refers to fluoro, chloro, bromo, or iodo. Similarly, the term "halogen" refers to fluorine, chlorine, bromine, and iodine.

The term "substituted" indicates that one or more hydrogen atoms on the group indicated in the expression using "substituted" is replaced with a "substituent". The number referred to by 'one or more' can be apparent from the moiety on which the substituents reside. For example, one or more can refer to, e.g., 1, 2, 3, 4, 5, or 6; in some embodiments 1, 2, or 3; and in other embodiments 1 or 2, and if the substituent is an oxo group, two hydrogen atoms are replaced by the presence of the substituent. The substituent can be one of a selection of indicated groups, or it can be a suitable group recited below or known to those of skill in the art, provided that the substituted atom's normal valency is not exceeded, and that the substitution results in a stable compound. Suitable substituent groups include, e.g., alkyl, alkenyl (e.g., vinyl, or allyl), alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, alkylcarbonyloxy, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkyl sulfonyl, arylsulfinyl, aryl sulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano, as well as the moieties illustrated in the schemes and Figures of this disclosure; or combinations thereof. Additionally, suitable substituent groups can be, e.g., —X, —R, —O⁻, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NRR, —S(=O)$_2$O⁻, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —OP(=O)(OH)(OR), —P(=O)(OH)(OR), —P(=O)(O⁻)$_2$, —P(=O)(OH)$_2$, —C(=O)R, —C(=O)X, —C(S)R, —C(O)OR, —C(O)O⁻, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, cycloalkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more substituents above can be excluded from the group of potential values for substituents on the substituted group. The various R groups in the schemes and figures of this disclosure can be one or more of the substituents recited above, thus the listing of certain variables for such R groups (including $R^1$, $R^2$, $R^3$, etc.) are representative and not exhaustive, and can be supplemented with and/or substituted by one or more of the substituents above.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" can include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject.

The term "cancer cell" is intended to encompass definitions as broadly understood in the art. In an embodiment, the term refers to an abnormally regulated cell that can contribute to a clinical condition of cancer in a human or animal. In an embodiment, the term can refer to a cultured cell line or a cell within or derived from a human or animal body. A cancer cell can be of a wide variety of differentiated cell, tissue, or organ types as is understood in the art. The cancer cells can result in the formation of a tumor. The term "tumor" refers to a neoplasm, typically a mass that includes a plurality of aggregated malignant cells. Cancer of varying types (e.g., those recited herein) and the resulting tumors can be treated by the atropisomers described herein.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof Such as racemic mixtures, form part of the present invention. Many organic compounds exist in optically active forms, i.e., they have the ability to rotate the plane of plane-polarized light. In describing an optically active compound, the prefixes D and L, or R and S. are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate (defined below), which may occur where there has been no stereoselection or stereospecificity in a chemical reaction or process.

The terms "racemic mixture" and "racemate" refer to an equimolar mixture of two enantiomeric species, devoid of optical activity.

The term "enantiomerically enriched" ("ee") as used herein refers to mixtures that have one enantiomer present to a greater extent than another. Reactions that provide one enantiomer present to a greater extent than another would therefore be "enantioselective" (or demonstrate "enantioselectivity"). In one embodiment of the invention, the term "enantiomerically enriched" refers to a mixture having at least about 2% ee; in another embodiment of the invention, the term "enantiomerically enriched" refers to a mixture having at least about 5% ee; in another embodiment of the invention, the term "enantiomerically enriched" refers to a mixture having at least about 20%; in another embodiment of the invention, the term "enantiomerically enriched" refers to a mixture having at least about 50%; in another embodiment of the invention, the term "enantiomerically enriched" refers to a mixture having at least about 80%; in another embodiment of the invention, the term "enantiomerically enriched" refers to a mixture having at least about 90%; in another embodiment of the invention, the term "enantiomerically enriched" refers to a mixture having at least about 95%; in another embodiment of the invention, the term "enantiomerically enriched" refers to a mixture having at least about 98%; in another embodiment of the invention, the term "enantiomerically enriched" refers to a mixture having at least about 99%. The term "enantiomerically enriched" includes enantiomerically pure mixtures which are mixtures that are substantially free of the species of the opposite optical activity or one enantiomer is present in very low quantities, for example, 0.01%, 0.001% or 0.0001%.

The term "atropisomers" refers to conformational stereoisomers that occur when rotation about a single bond in the molecule is prevented, or greatly inhibited, as a result of steric interactions with other parts of the molecule and the substituents at both ends of the single bond are asymmetrical, i.e., optical activity arises without requiring an asymmetric carbon center or stereocenter. Where the rotational barrier about the single bond is high enough, and interconversion between conformations is slow enough, separation and isolation of the isomeric species is often achievable by standard separation techniques such as HPLC. Atropisomers are enantiomers without requiring a single asymmetric atom. Atropisomers are considered stable if the barrier to interconversion is high enough to permit the atropisomers to undergo little or no interconversion at room temperature for at least a week, preferably at least a year. In some embodiments, an atropisomeric compound as described herein does not undergo more than about 5% interconversion to its opposite atropisomer at room temperature during one week when the atropisomeric compound is in substantially pure form, which is generally a solid state. In some embodiments, an atropisomeric compound does not undergo more than about 5% interconversion to its opposite atropisomer at room temperature (approximately 25° C.) for one year. Preferably, the atropisomeric compounds are stable enough to undergo no more than about 5% interconversion in an aqueous pharmaceutical formulation held at 0° C. for at least one week.

The energy barrier to thermal racemization of atropisomers can be determined by the steric hindrance to free rotation of a bonds forming a chiral axis. Some biaryl compounds exhibit atropisomerism where rotation around an interannular bond lacking C2 symmetry is restricted. The free energy barrier for isomerization (enantiomerization) is a measure of stability of the interannular bond with respect to rotation. Optical and/or thermal excitation can promote racemization of such isomers, dependent on electronic and steric factors.

The term "conformationally stable atropisomer" or "atropisomerically stable" refers to an atropisomer that is conformationally stable such that it has a barrier to rotation of at least about 5 kcal/mol, at least about 15 kcal/mol, or at least about 25 kcal/mol (at a temperature of about 25° C. to about 35° C.). The stability of a conformationally stable atropisomer is such that its $t_{1/2}$ at an elevated temperature (e.g., 37° C.) is at least about 8 hours, at least about 10 days, at least about 12 days, at least about 15 days, at least about 18 days, at least about 150 days, or at least about 300 days. A conformationally stable atropisomer is thus a stereochemically stable at room temperature, e.g., to provide an atropisomer having atropisomeric purity.

The term "atropisomerism rotational blocking moiety" is a group that, when covalently bonded to a rotatable phenyl moiety of a kinase inhibitor, increases the barrier to rotation of the phenyl moiety such that the molecule becomes an atropisomer that is conformationally stable, as described above.

The term "Michael acceptor" is a type of electrophile that can reaction with a nucleophile to form a covalent bond, such as an activated unsaturated alkyl moiety wherein said moiety is activated by an electron withdrawing group. An example is but is not limited to an enone. Persons of skill in the art recognize the various types of Michael acceptors.

The steric size of the N-substitution ($R^1$) of Formula I can have an effect on the barrier to rotation. This is a manifestation of 'the buttress effect' (Bringmann et al., *Angew. Chemie Int. Ed.* 2005, 44, 5384-5427) and represents a strategy to increase stereochemical stabilities.

The term "irreversible inhibitor" refers to an inhibitor that will bind to a target such as an enzyme so that no other enzyme-substrate complexes can form. Irreversible inhibitors react with the target and change it chemically (e.g. via covalent bond formation). These inhibitors modify key amino acid residues needed for biological activity. In contrast, reversible inhibitors bind non-covalently.

Hyperinflammatory diseases refer to viral or bacterial-induced immune response, for example COVID-19, and autoimmune disorders for example rheumatoid arthritis.

Embodiments of the Invention

This disclosure provides an atropisomer compound of Formula I:

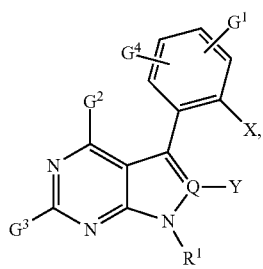

(I)

or
an enantiomer, diastereomer, salt, or solvate thereof;
wherein
$G^1$ is aryloxy, halo, hydroxy, alkyl, alkoxy, amino, amido, nitro, or phenyl;
$G^2$ is amino, halo, hydroxy, alkyl, alkoxy, aryloxy, amido, nitro, or phenyl;
$G^3$ and $G^4$ are independently H, halo, hydroxy, alkyl, alkoxy, nitro, or amino;
Q is C or N;
X and Y taken together form an atropisomerism rotational blocking moiety; and
$R^1$ is a buttressing substituent wherein the buttressing substituent comprises a ring heteroatom and an electrophile;
wherein the atropisomer is atropisomerically stable.

In various embodiments, amido is —(C=O)NR$^a$R$^b$ wherein R$^a$ and R$^b$ are each independently H, —(C$_1$-C$_6$)alkyl, —(C$_1$-C$_6$)cycloalkyl, aryl, or heterocycle. In some embodiments, aryl is unsubstituted or substituted phenyl. In some other embodiments, heterocycle is unsubstituted or substituted pyridyl. In some embodiments the electrophile is, for example, a Michael acceptor or an alkyl halide. In additional embodiments, the substituent comprising a ring heteroatom is, for example but not limited to, piperazine, piperidine, pyrrolidine, pyrrole, pyridine, pyrazine, a pyran, or a furan.

Also, this disclosure provides an atropisomer compound of Formula IB:

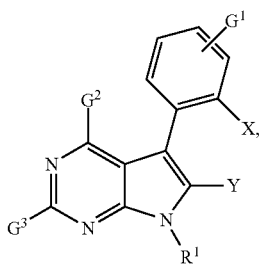

(IB)

or
an enantiomer, diastereomer, salt or solvate thereof;
wherein
$G^1$, $G^2$ and $G^3$ are each independently halo alkyl, alkoxy, amino, or phenyl;
X and Y taken together form an atropisomerism rotational blocking moiety; and
R is a buttressing substituent;
wherein the atropisomer is atropisomerically stable.

In various embodiments, the selectivity of the atropisomer is modulated compared to a corresponding rapidly interconverting parent kinase inhibitor, wherein the atropisomerism rotational blocking moiety of the atropisomer in combination with the buttressing substituent form a barrier to rotation of at least 10 kcal/mol, and the atropisomeric purity of the atropisomer has a half-life of at least 8 hours, thereby stabilizing atropisomerism of the atropisomer having modulated kinase selectivity. It is noted that the rapidly interconverting parent kinase inhibitor would be a compound of Formula I wherein, for example X and Y are both H, or one of X and Y is H (e.g., X is H or Y is H). In various additional embodiments, the modulated atropisomer binds more selectively and/or has higher affinity to a particular kinase target/receptor (e.g., BTK) than the parent kinase inhibitor.

In various additional embodiments, the buttressing substituent is capable of covalently binding (via the electrophile) to a nucleophile, such as an oxygen, sulfur, or nitrogen atom of, for example, a protein or enzyme.

In some embodiments Y is a lone pair of electrons when Q is N. In some embodiments X is not H, or Y is not H. In various embodiments X and Y are not H. In additional embodiments, X is sufficiently large to sterically interact with Y, Y is sufficiently large to sterically interact with X, or both X and Y are sufficiently large to sterically interact with each other such that X and Y together hinder or block full 360 degree rotation about the C—C covalent bond joining the aryl moiety and the pyrrolopyrimidine moiety in Formula I. In other embodiments, the buttressing substituent ($R^1$) increases the steric interaction between substituents X and Y to hinder or block said 360 degree rotation.

In some embodiments, the compound is an atropisomer having an (R)-configuration in reference to the bond joining the phenyl moiety and the heterocyclic moiety of Formula I (based on Cahn-Ingold-Prelog priority rules—R$_a$ is analogous to R). In some embodiments, the compound is an atropisomer having an (S)-configuration in reference to the bond joining the phenyl moiety and the heterocyclic moiety of Formula I (based on Cahn-Ingold-Prelog priority rules—S$_a$ is analogous to S). In some embodiments, the compound is a (+)-atropisomer (dextrorotatory rotation of polarized light). In some embodiments, the compound is a (−)-atropisomer (levorotatory rotation of polarized light). In some other embodiments, $R^1$ has at least one chiral center. In some embodiments, $R^1$ is a heterocycle, wherein the heterocycle is optionally substituted. In other embodiments, $R^1$ is a nitrogen heterocycle wherein the nitrogen heterocycle is substituted with a Michael acceptor. In additional embodiments, $R^1$ is:

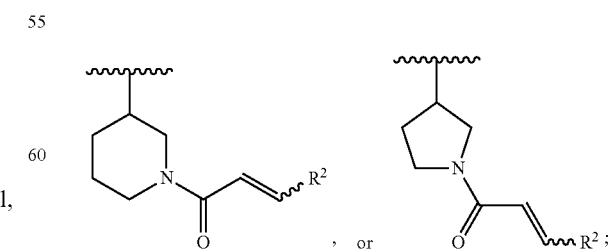

wherein $R^2$ is H, halo, nitro, amide, carboxylic acid, ester, or —(C$_1$-C$_6$)alkyl.

In other embodiments, X is —(C$_1$-C$_6$)alkyl, halo, hydroxy, —O(C$_1$-C$_6$)alkyl, or amino. In yet other embodiments, Q is C. In further embodiments, Y is —(C$_1$-C$_6$)alkyl, halo, hydroxy, —O(C$_1$-C$_6$)alkyl, or amino, wherein —(C$_1$-C$_6$)alkyl is optionally substituted with one or more substituents described in the definitions above.

In other embodiments, G$^1$ is —(C═O)NHpyridyl. In various embodiments, G$^1$ is OPh, or —(C═O)NR$^a$heteroaryl wherein R$^a$ is H or —(C$_1$-C$_6$)alkyl. In some embodiments, heteroaryl is 2-pyridyl, 3-pyridyl, or 4-pyridyl. In other embodiments, the pyridyl moiety or heteroaryl moiety of the amido group is substituted with one or more substituents described in the definitions above. In some other embodiments, G$^2$ is NH$_2$. In other embodiments, amino is substituted with —(C$_1$-C$_6$)alkyl. In yet other embodiments, G$^3$ is H. In other embodiments, G$^4$ is H, F, or CH$_3$. In various other embodiments, X and Y are —(C$_1$-C$_6$)alkyl or CH$_3$.

In other embodiments, the compound of Formula I is a compound of Formula II or Formula IIB:

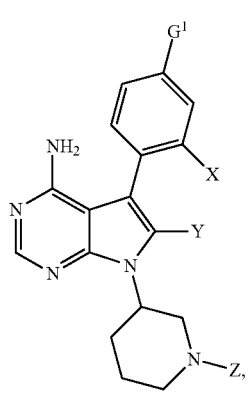

(II)

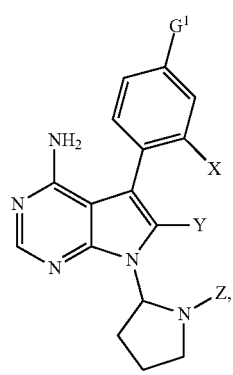

(IIB)

or an enantiomer or diastereomer thereof; wherein

G$^1$ is aryloxy or amido;

X is halo alkyl, alkoxy, or amino;

Y is halo alkyl, alkoxy, or amino; and

Z is alkyl or acyl.

In various embodiments, acyl is —(C═O)(C$_1$-C$_6$)alkyl wherein the (C$_1$-C$_6$)alkyl moiety is unsaturated or saturated and optionally substituted with substituents described herein.

In additional embodiments, Z is:

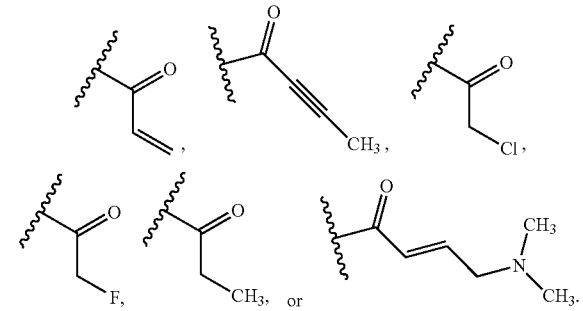

Note that in this disclosure, the wiggly line that is orthogonal to a bond refers to a point of attachment. For example, the C═O moiety of Z is bonded to the nitrogen atom of the N—Z moiety of Formula II.

In yet other embodiments, the compound is:

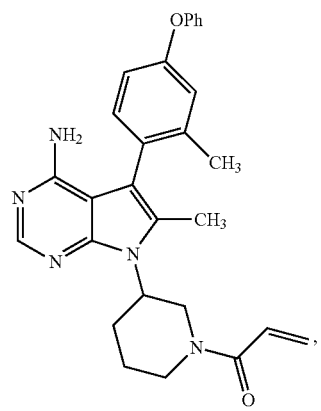

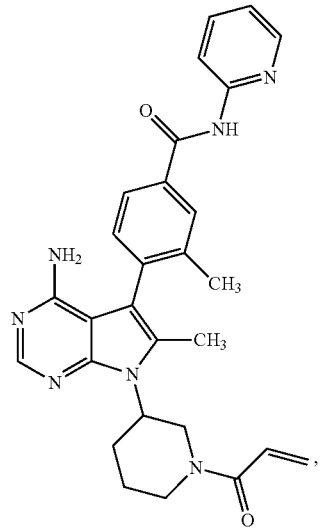

or an enantiomer or diastereomer thereof.

In some embodiments, the compound is:

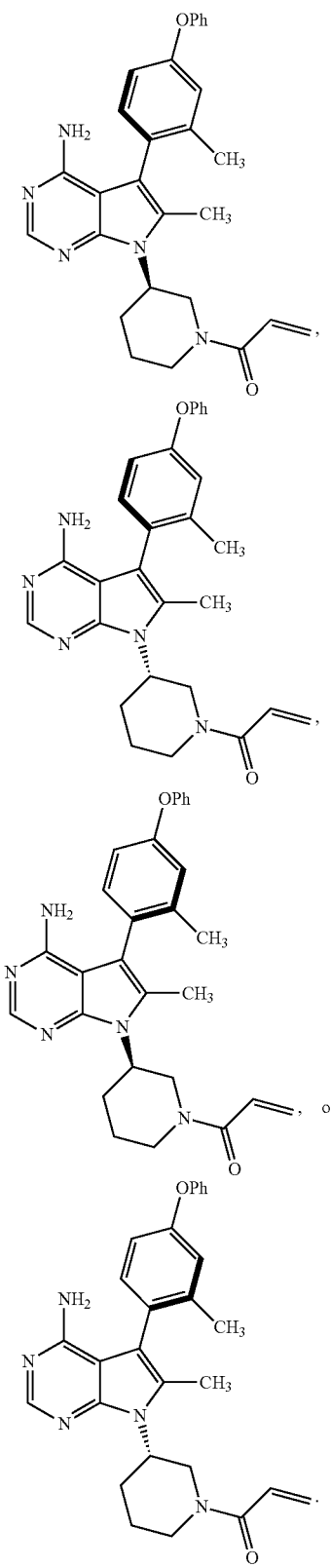

The bolded bonds at the side of the phenyl group (e.g., >) indicate the side that is above the plane of the pyrimidoin- dole heterocycle to indicate the stereochemical configuration of the atropisomer. In some embodiments, the atropisomer compound has the configuration $(S_a,S)$, $(R_a,R)$, $(S_a,R)$, or $(R_a,S)$.

In additional embodiments, each atropisomer when isolated/purified has a atropisomeric purity of at least 90%, at least 95%, at least 99%, or at least 99.9%. In other embodiments, said percent atropisomeric purity is the atropisomeric purity after initial isolation/purification, wherein the atropisomeric purity remains about the same for at least: 1 year, 6 months, 1 month, 10 days, 1 week, or 2 days.

In additional embodiments, the compound of Formula I is a compound of Formula III-V:

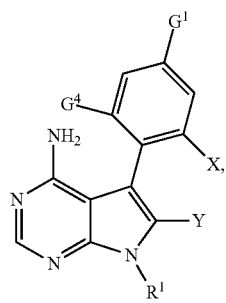
(III)

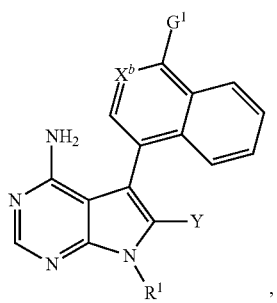
(IV)

, or

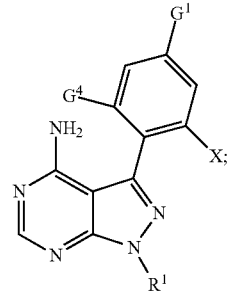
(V)

wherein
$X^b$=CH, N;

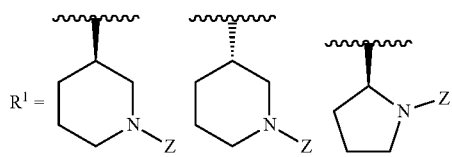

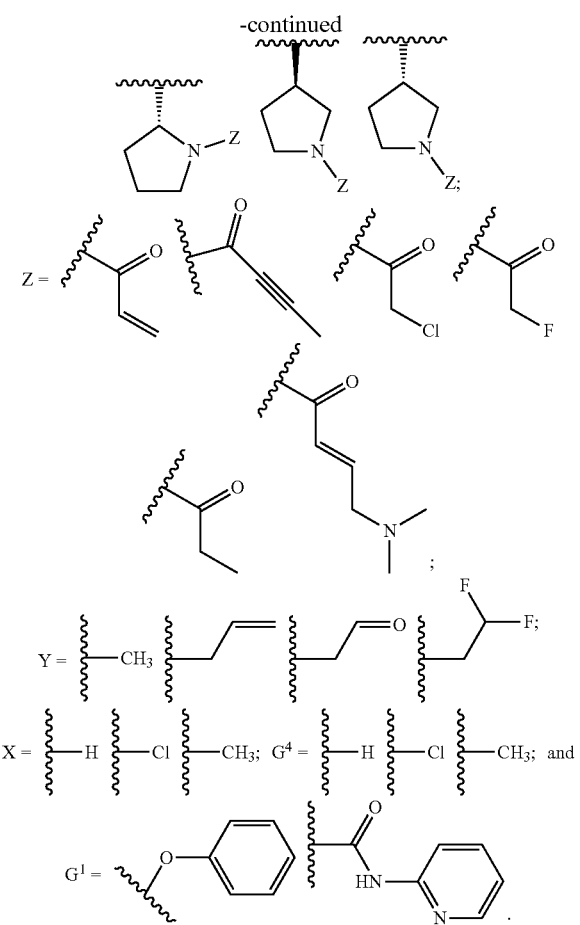

This disclosure provides, a pharmaceutical composition comprising the compound above in combination with a pharmaceutically acceptable diluent, carrier, or excipient.

This disclosure also provides a method of inhibiting the growth of cancer cells comprising contacting cancer cells with an effective amount of an atropisomer of the compound above, thereby inhibiting the growth of the cancer cells. In some embodiments, the contacting is in vivo or in vitro.

In various embodiments, the atropisomer is selective for BTK kinase over other kinases. In some embodiments, the selectivity for BTK kinase in terms of $IC_{50}$ is about 2× to about 1000× the $IC_{50}$ for another kinase. In other embodiments, the selectivity is about 10×, about 50×, about 100×, about 250×, about 500×, or about 750×. In further embodiments, the atropisomer irreversibly binds and inhibits BTK kinase. In other various embodiments, the cancer cells are breast cancer cells, lung cancer cells, pancreatic cancer cells, prostate cancer cells, colon cancer cells, blood cancer cells, or thyroid cancer cells.

This disclosure also provides a method for the treatment of cancer in a subject in need thereof comprising administering an effective amount of the compound disclosed herein, or a combination of said compound in combination with a second agent, thereby treating the cancer. In some embodiments the second agent is an inhibitor of cancer or is an anticancer agent.

This disclosure additionally provides use of the compound above for the treatment of a cancer comprising administering to a subject having cancer a therapeutically effective amount of the compound, thereby treating the cancer in the subject.

Additionally, this disclosure provides method for the treatment of exaggerated hyperinflammatory responses such as COVID-19 and/or rheumatoid arthritis in a subject in need thereof comprising administering an effective amount of the compound disclosed herein, or a combination of said compound in combination with a second agent, thereby treating the inflammatory responses associated with COVID-19 and/or rheumatoid arthritis.

Atropisomeric Compounds and Selectivity

There are over 500 kinases in the human genome and their aberrant activity can lead to life threating diseases. Most kinase inhibitors contain a dynamic form of chirality known as atropisomerism. While these molecules are not always considered chiral, they will interact with their target in an enantioselective fashion, with the non-relevant atropisomer contributing little to the desired activities. Herein, we design and synthesize atropisomeric analogs of a known promiscuous kinase inhibitor, Ibrutinib, to reduce the off-target inhibition associated with Ibrutinib. Through a conformational analysis of the atropisomeric analogs, we found the methyl used to lock the atropisomeric axis also influenced the low energy conformations of the adjacent piperidine chair, leading to the synthesis of a total of 4 diastereomeric analogs of Ibrutinib.

Figure 3:
FIG. 3. Atropisomerism and Kinase Selectivity.
Figure 3:
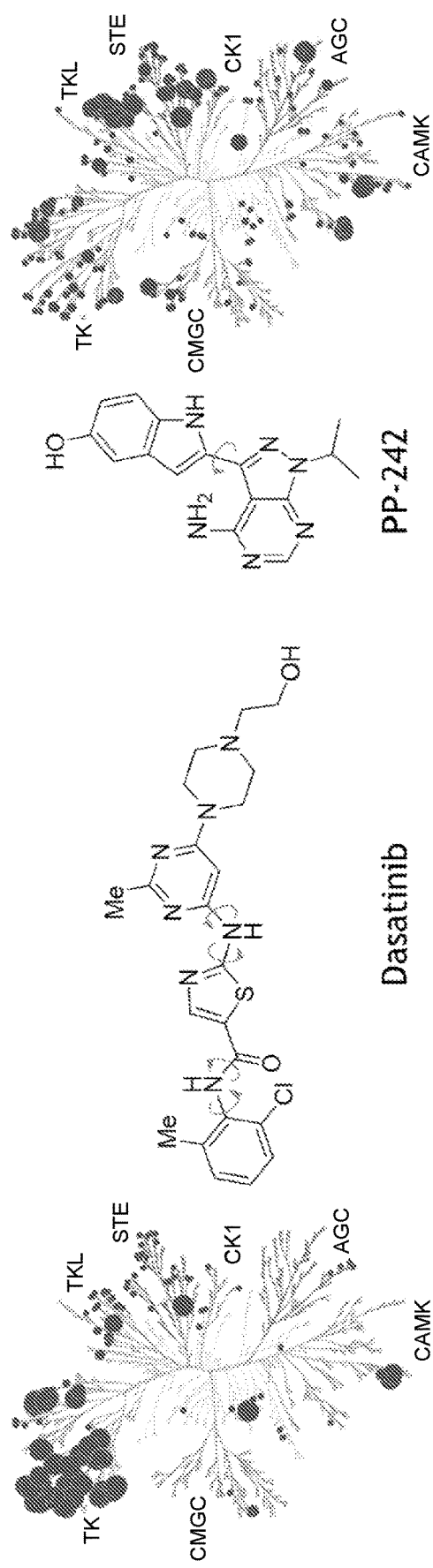

Atropisomerism is an extended form of chirality that arises from the hindered rotation about a chiral axis. If the substitution proximal to the atropisomeric axis is large enough, the resulting atropisomers can be isolated and characterized. We found that 82% of FDA approved kinase inhibitors exhibit an atropisomeric axis, however the vast majority of these exist as a rapidly interconverting mixture of enantiomers. When kinase inhibitors bind to an active site, they do so in atroposelective fashion. While one rotational conformer binds to the target active site, the other conformer often contributes to off target activity, potentially leading to unintended side effects (FIG. 3).

Figure 4:
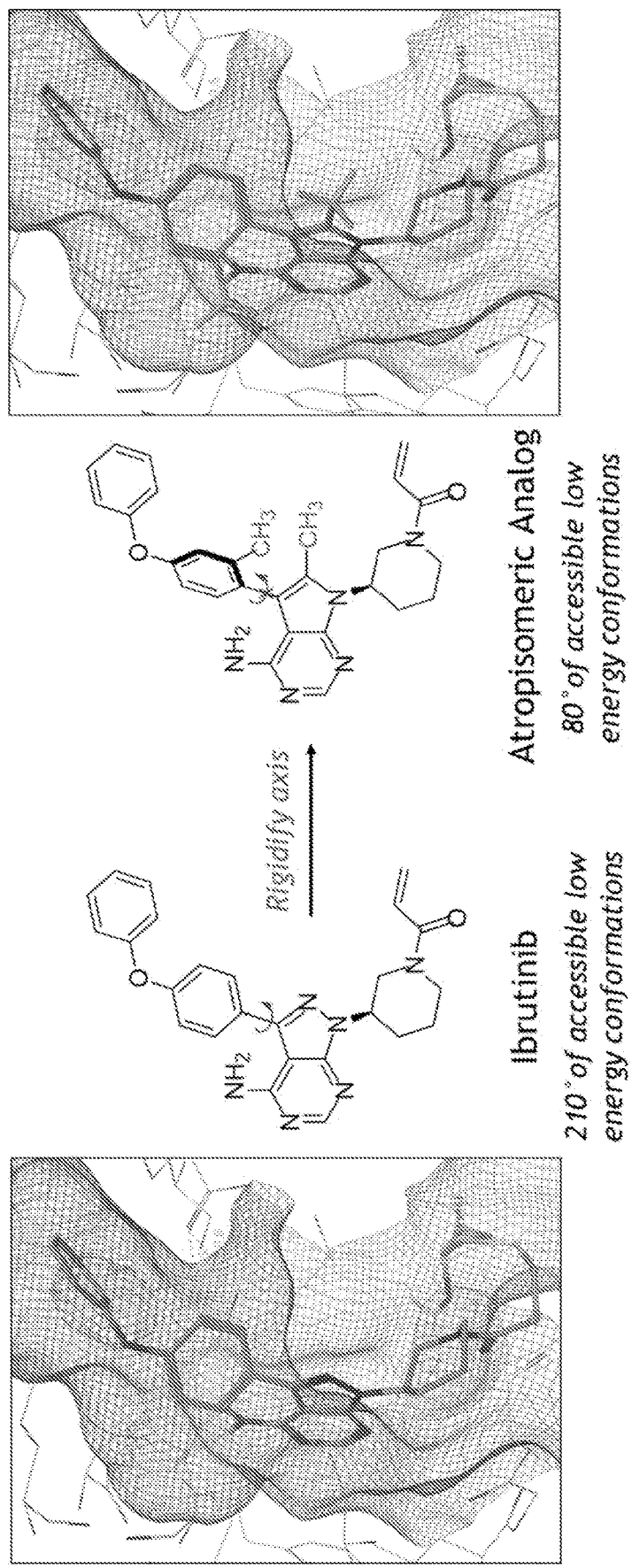
FIG. 4. Atropisomerism as a Selectivity Filter.

Ibrutinib is an FDA-approved Bruton's tyrosine kinase (BTK) inhibitor used to treat various types of leukemia and lymphoma. Ibrutinib inhibits BTK by covalently targeting BTK's nucleophilic Cysteine 481 with its acrylamide motif Ibrutinib, however, is not selective and binds other kinases with cysteine residues found in the similar positions (i.e. EGFR, ITK, BLK, etc.). This promiscuity leads to well characterized side-effects. We hypothesize that by rigidifying Ibrutinib's pro-atropisomeric axis we can increase the selectivity of new Ibrutinib analogs (FIG. 4).

Figure 5:
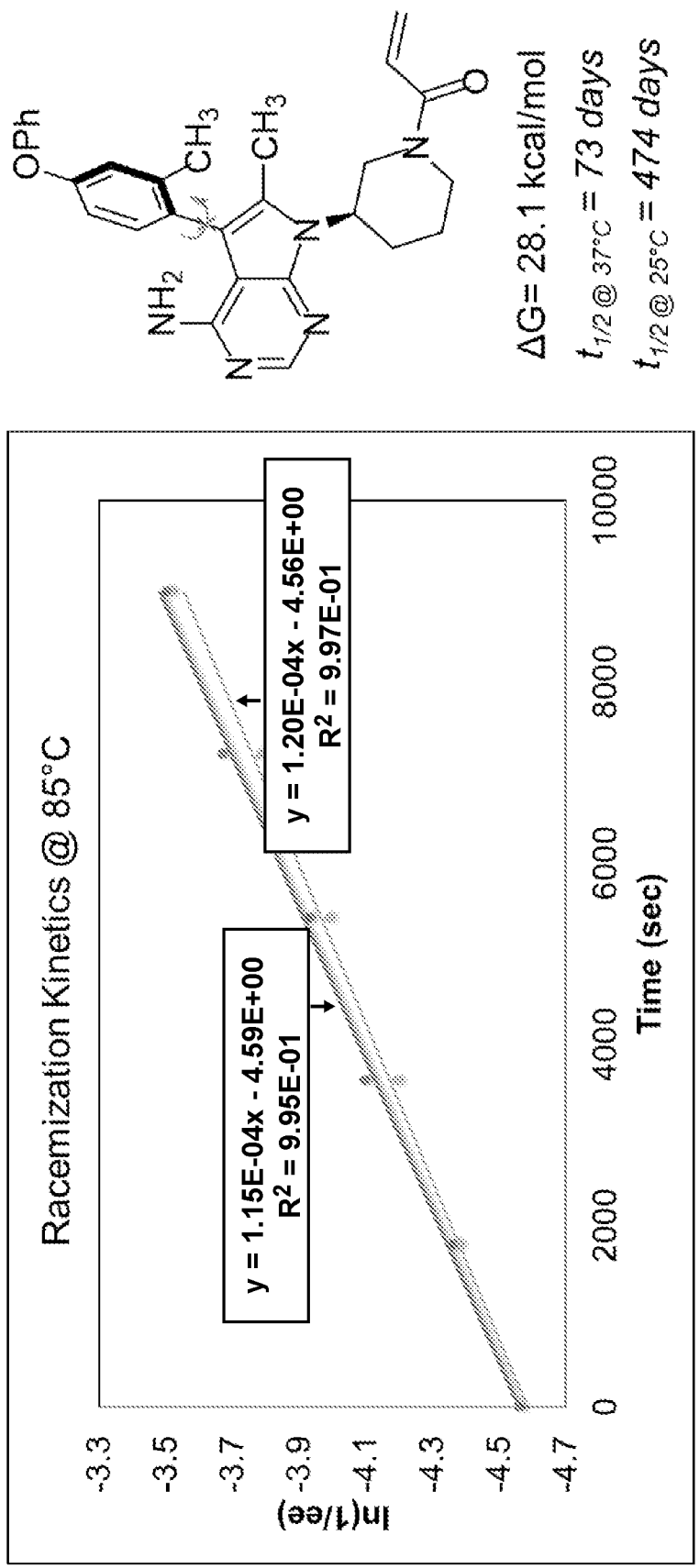
FIG. 5. Barrier to rotation studies.

After separating both stable atropisomers on a chiral phase HPLC column, we tested the stereochemical stability of the atropisomerically pure compound. This was accomplished by heating an enantiopure compound at 85° C. and analyzing the rate of racemization over the course of ~3 hours. Using Eyring's equation, the ΔG was determined to be 28.1 kcal/mol (FIG. 5).

Figure 2:
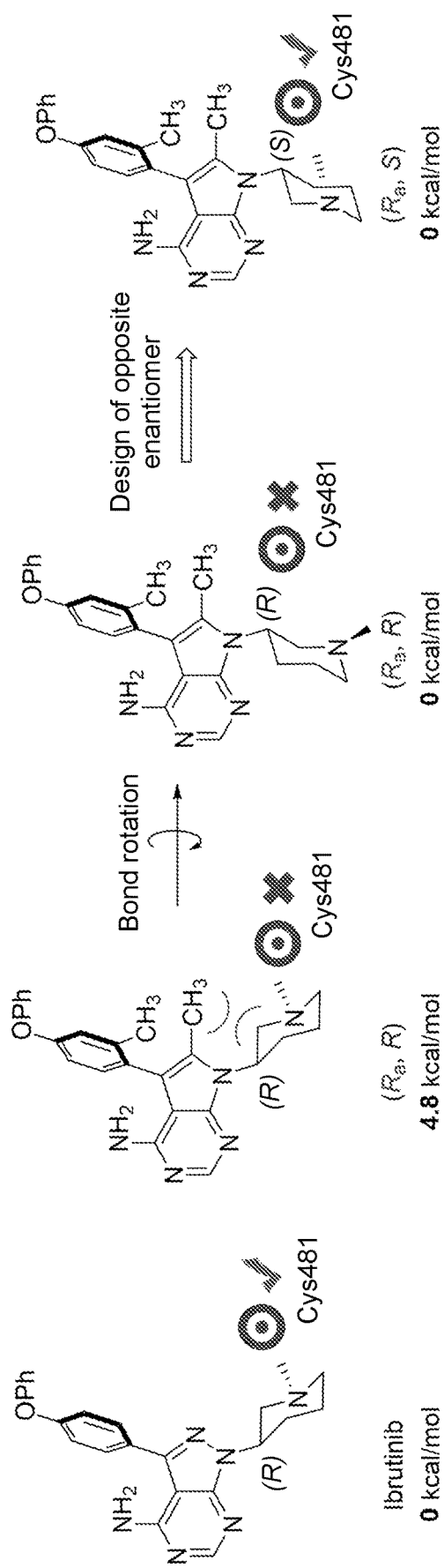
FIG. 2. Conformational control of piperidine. Analysis of the inhibitors' conformations predicted allylic strain when incorporating the C-2 methyl group which leads to a bond rotation that positions the acrylamide out of Cys481's range. This led to the synthesis of the opposite S enantiomer where the same bond rotation instead directs the acrylamide toward Cys481.

We first synthesized the atropisomeric analogs of Ibrutinib with the same piperidine enantiomer (R). However, molecular docking studies suggest the acrylamide must be pointed in a certain direction to engage Cys481. Analysis of the inhibitors' conformations predicted allylic strain when incorporating the C-2 methyl group which leads to a bond rotation that positions the acrylamide out of Cys481's range. This led to the synthesis of the opposite S enantiomer where the same bond rotation instead directs the acrylamide toward Cys481 (FIG. 2).

Out of the atropisomeric analogs tested, (Ra, S) possessed the highest affinity towards BTK, 10× more potent than the diastereomer (Ra, R) suggesting the piperidine conformation plays a major role in binding affinity. While less potent than Ibrutinib, (Ra, S) displayed increased selectivity for BTK over each of the tested kinases (Table 1).

TABLE 1

In Vitro Kinase Assay Data

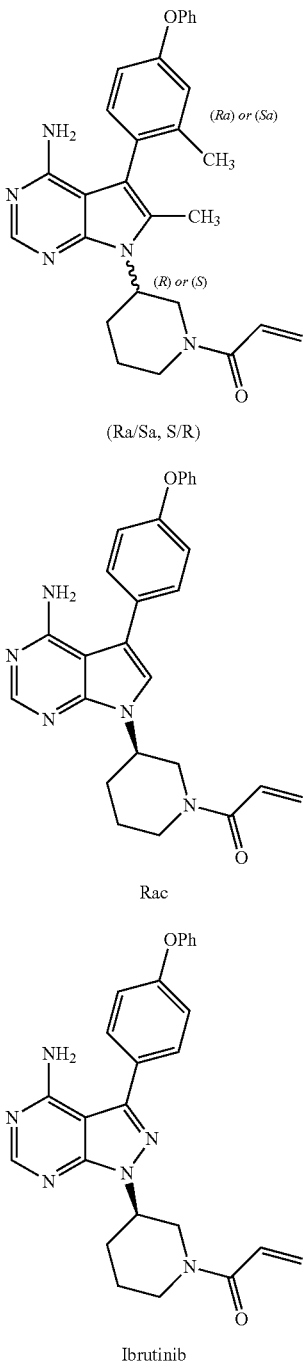

| Kinase IC$_{50}$ (nM) | (Ra, S) | (Ra, R) | (Sa, R) | (Sa, S) | Rac | Ibrutinib |
|---|---|---|---|---|---|---|
| BTK | 425 | 3307 | >10000 | 3923 | 0.47 | 1.5 |
| HER2 | >10000 | >10000 | >10000 | >10000 | 451 | 6.4 |
| ITK | >10000 | >10000 | >10000 | >10000 | — | 4.9 |
| BLK | 187 | 1814 | 9964 | 1732 | 0.29 | 0.1 |

Conformational Binding Map

To explain increases in selectivity, we generated a map that reveals a kinase's preferred pyrrolopyrimidine (PPY) or pyrazolopyrimidine (PP) binding inhibitor conformation using Protein Data Bank (PDB) co-crystal structures (FIG. 1, columns). When superimposing the calculated the conformational energy plots (CEPs) of the different inhibitors, we observed the increase in selectivity originates from the narrowing of rigid, atropisomer inhibitor's accessible conformations to a window covering a preferred binding dihedral angle. BTK bound its inhibitors in a region around −120° suggesting this strategy of confining an inhibitor's conformational space near orthogonality via stable atropisomerism could be amenable to BTK. In addition, both Ibrutinib and Acalabrutinib possess an atropisomeric PP scaffold, so their structures can serve as a guide for our inhibitor optimization and can be represented in the PP/PPY conformational binding map.

Development of Atropisomerically Stable Analogs of Ibrutinib

We have developed preorganized analogs of ibrutinib that sample a range of conformational space to extend our strategy to a new target, BTK. During inhibitor optimization, we encountered unintended consequences when incorporating steric bulk to this scaffold and developed ways to circumvent these issues. To begin, we analyzed the binding pockets of four PDB BTK structures co-crystalized with freely rotating, unsubstituted PP/PPY ligands (FIG. 1). Two key observations where made: 1) Each ligand bound BTK with its atropisomeric dihedral angle between −123.98° and −119.57° and 2) there is a hydrophobic cavity near each ligands' aryl ortho position. This suggests that BTK would have an atropisomeric preference to bind the (R$_a$)-atropisomer with a hydrophobic substituent orientated in the −180°-0° dihedral angle range. We also noticed the PP nitrogen (N-2), ortho to Ibrutinib atropisomeric axis, is directed towards a conserved space, vacant of BTK amino acids. Incorporation at this site, in combination with an aryl ortho substituent, would likely rigidify the axis generating two separable atropisomers each possessing narrower CEP than Ibrutinib's (FIG. 1), with the (R$_a$)-atropisomer's CEP in range of BTK's −120° preferred dihedral angle. Thus, the proposed rigid analog's selectivity could be enhanced as its unable to access less orthogonal conformations preferred by other kinases.

General Synthetic Methods

The invention also relates to methods of making the compounds and compositions of the invention. The compounds and compositions can be prepared by any of the applicable techniques of organic synthesis, for example, the techniques described herein. Many such techniques are well known in the art. However, many of the known techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure*, 5$^{th}$ Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of the compounds of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically, the temperatures will be −100° C. to 200° C., solvents will be aprotic or protic depending on the conditions required, and reaction times will be 1 minute to 10 days. Work-up typically consists of quenching any unreacted reagents followed by partition between a water/organic layer system (extraction) and separation of the layer containing the product.

Oxidation and reduction reactions are typically carried out at temperatures near room temperature (about 20° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and will be applied when applicable.

Protecting Groups. The term "protecting group" refers to any group which, when bound to a hydroxy or other heteroatom prevents undesired reactions from occurring at this group and which can be removed by conventional chemical or enzymatic steps to reestablish the hydroxyl group. The particular removable protecting group employed is not always critical and preferred removable hydroxyl blocking groups include conventional substituents such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

Suitable hydroxyl protecting groups are known to those skilled in the art and disclosed in more detail in T. W. Greene, *Protecting Groups In Organic Synthesis*; Wiley: New York, 1981 ("Greene") and the references cited therein, and Kocienski, Philip J.; *Protecting Groups* (Georg Thieme Verlag Stuttgart, New York, 1994), both of which are incorporated herein by reference.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis.

Pharmaceutical Formulations

The compounds described herein can be used to prepare therapeutic pharmaceutical compositions, for example, by combining the compounds with a pharmaceutically acceptable diluent, excipient, or carrier. The compounds can be a single atropisomer, such as the atropisomers described herein. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, and 1) quantification of tumor cell kill, and the biological significance of the use of transplantable tumor screens are known; or 2) quantification of decreased immune cell activity and cytokine production, and the biological significance of the use of immune stimulation in mice models are known.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Ibrutinib Analog Synthesis

To incorporate substituents at the 2 position, we moved to the PPY scaffold which contains a functionalizable C—H in place of the PP scaffold's N-electron lone pair. Synthesis of the PPY scaffold begins with subjecting 2-(4,6-dichloropyrimidin-5-yl)acetaldehyde to MeMgI via Grignard addition (Scheme 1). After oxidizing the alcohol to a ketone with Dess-Martin periodinane, the ketone underwent a cyclodehydration+$S_NAr$ with N-boc-protected 3-aminopiperidine at 80° C. in DME in the presence of TEA to afford the cyclized pyrrolopyrimidine scaffold with a C-2 methyl. For unsubstituted C-2 PPYs, N-boc-protected 3-aminopiperidine was reacted in the same manner with the aldehyde as starting material instead of the ketone. Iodination at C-3 followed by Suzuki-Miyaura cross-coupling to corresponding boronic esters, yielded C-3 aryl PPYs. The aryl boronic esters were synthesized starting with para bromination of m-cresol or phenol under conditions listed in Scheme 1. A Chan Lam reaction with phenyl boronic acid afforded brominated diaryl ethers. Subsequent Miyaura borylation yielded the boronic esters that served as starting materials for the Suzuki-Miyaura cross-coupling step to the PPY. Addition of 2,4-dimethoxy benzylamine at elevated temperatures yielded a di-protected (piperidine N-boc and C-4 N-bzn) PPY containing a nitrogen at the C-4 position. Following deprotection with TFA, the crude material was added to acryloyl chloride yielding the final pyrrolopyrimidine inhibitors. If the inhibitor was atropisomerically stable, the racemic mixture was separated by chiral-phase HPLC.

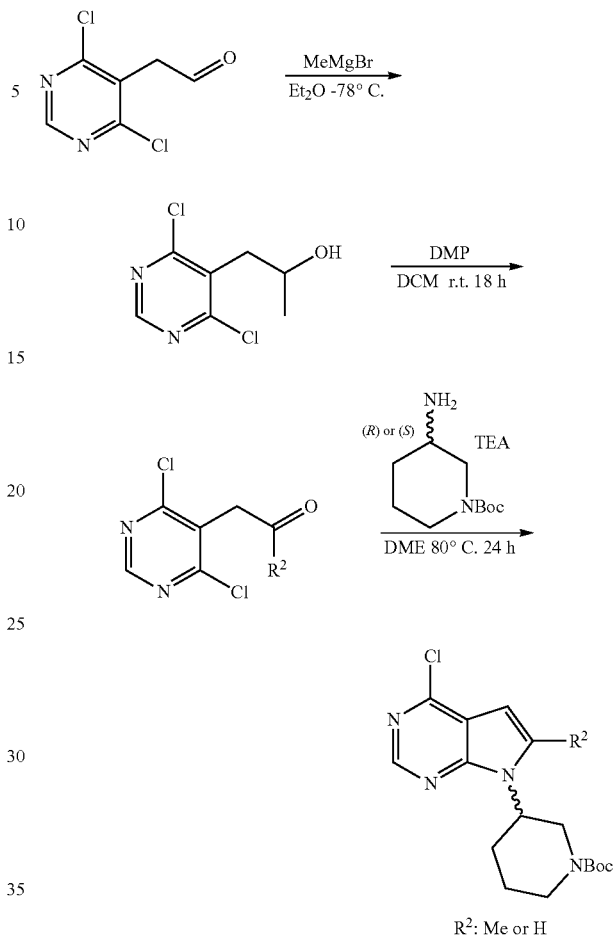

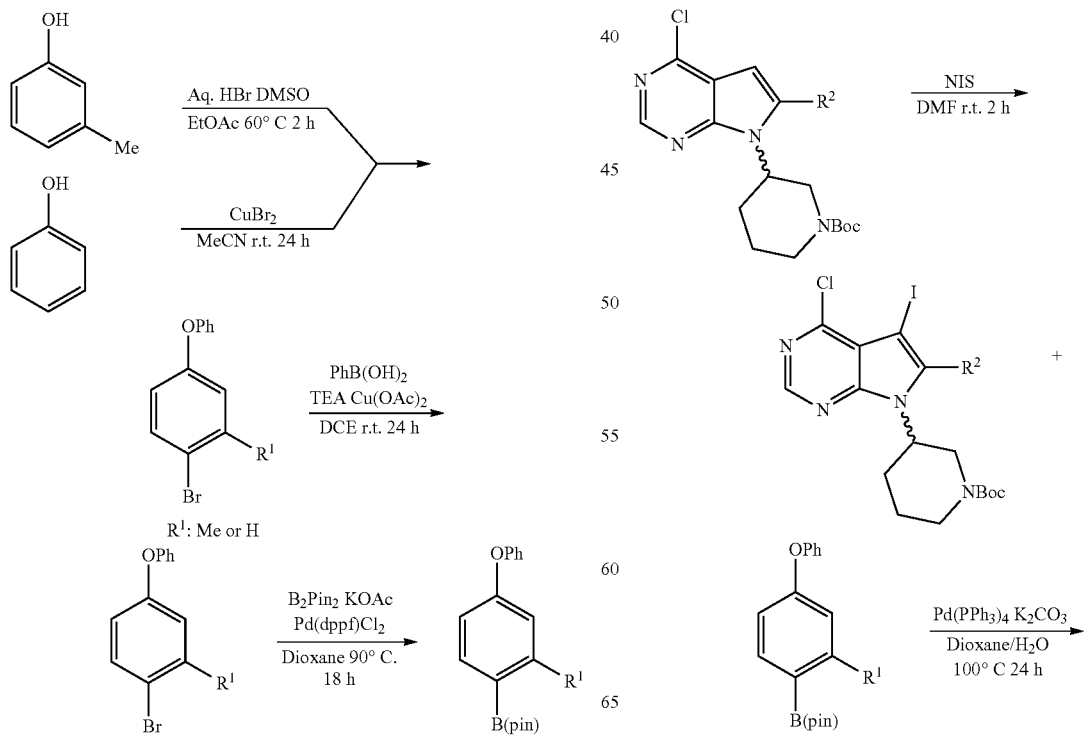

Scheme 1. Synthesis of pyrrolopyrimidine compounds 3.1 - 3.6.

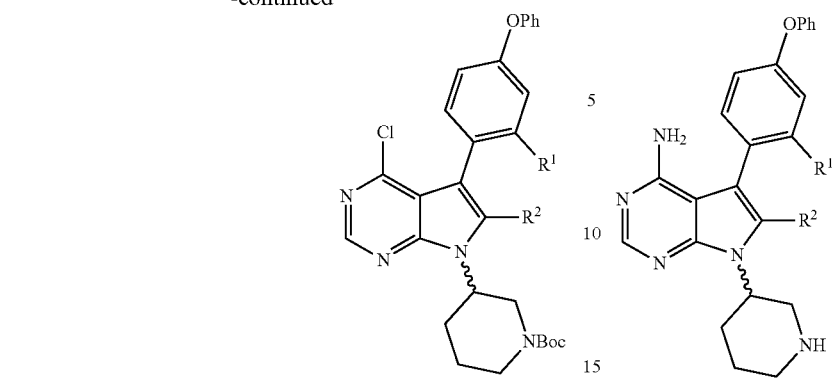

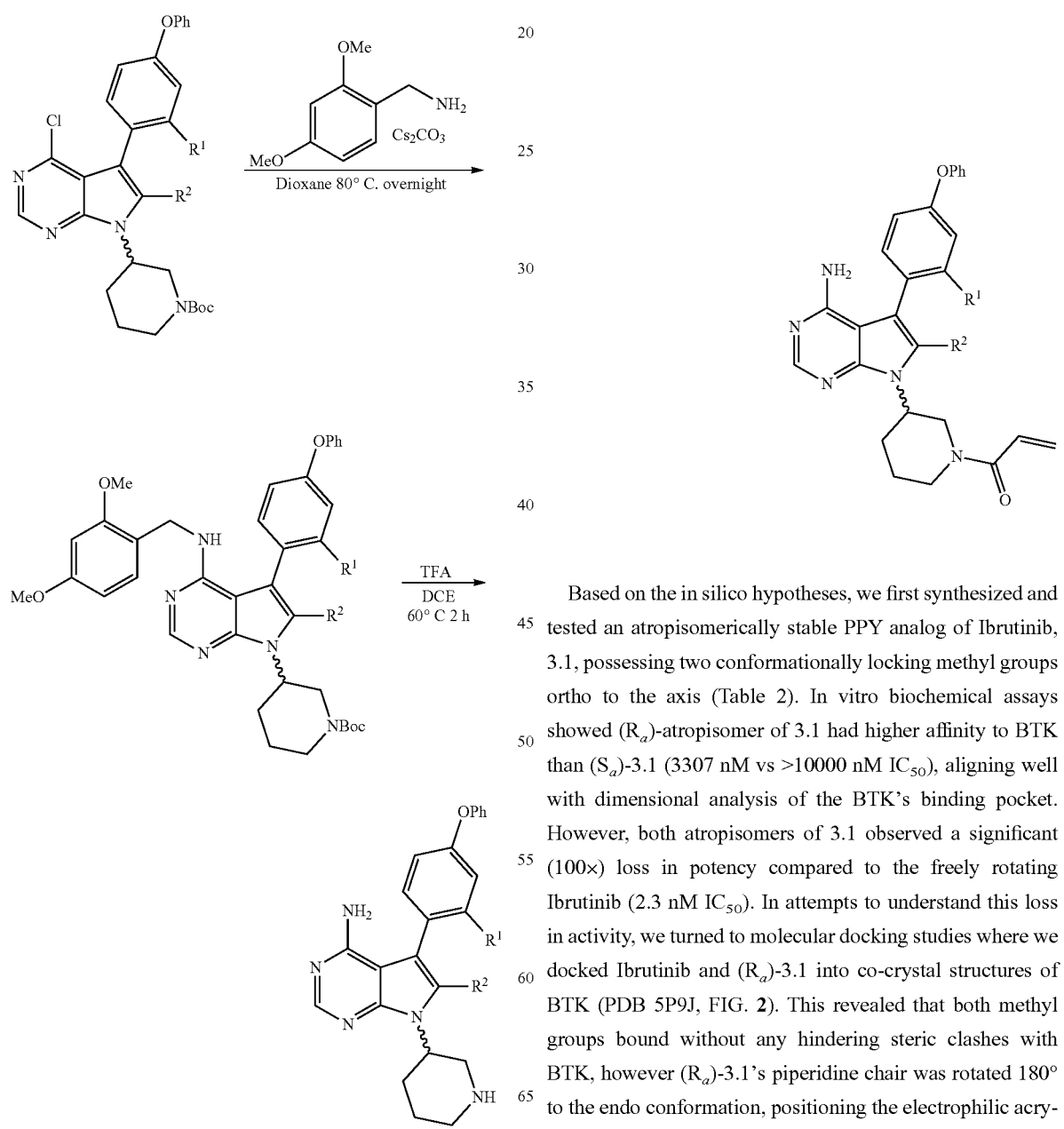

Based on the in silico hypotheses, we first synthesized and tested an atropisomerically stable PPY analog of Ibrutinib, 3.1, possessing two conformationally locking methyl groups ortho to the axis (Table 2). In vitro biochemical assays showed ($R_a$)-atropisomer of 3.1 had higher affinity to BTK than ($S_a$)-3.1 (3307 nM vs >10000 nM $IC_{50}$), aligning well with dimensional analysis of the BTK's binding pocket. However, both atropisomers of 3.1 observed a significant (100×) loss in potency compared to the freely rotating Ibrutinib (2.3 nM $IC_{50}$). In attempts to understand this loss in activity, we turned to molecular docking studies where we docked Ibrutinib and ($R_a$)-3.1 into co-crystal structures of BTK (PDB 5P9J, FIG. 2). This revealed that both methyl groups bound without any hindering steric clashes with BTK, however ($R_a$)-3.1's piperidine chair was rotated 180° to the endo conformation, positioning the electrophilic acrylamide in the opposite direction of the nucleophilic Cys841.

TABLE 2

Kinase inhibition data for Ibrutinib (compounds 3.1 and 3.2)

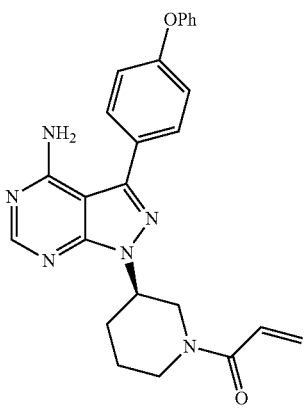 [SMILES: C=CC(=O)N1CCC[C@@H](n2nc(-c3ccc(Oc4ccccc4)cc3)c3c(N)ncnc32)C1]

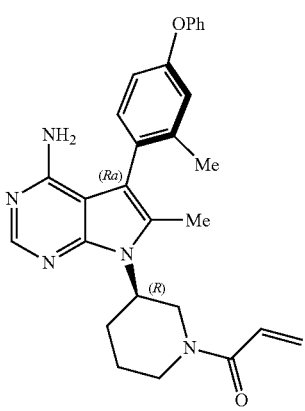

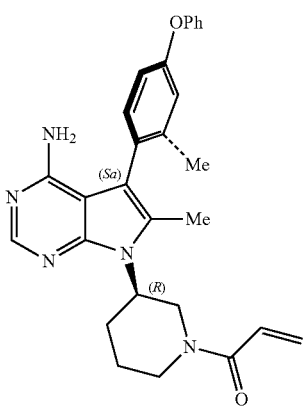

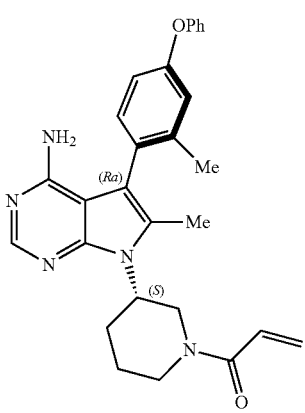

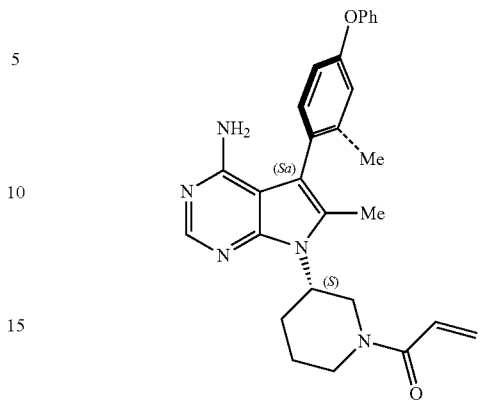

| Kinase IC$_{50}$ (nM) | Ibrutinib | (Ra)-3.1 | (Sa)-3.1 | (Ra)-3.2 | (Sa)-3.2 |
|---|---|---|---|---|---|
| BTK | 2.3 | 3307 | >10000 | 425 | 3923 |
| BLK | 8.1 | 1814 | 9964 | 187 | 1732 |

To verify this result, we analyzed the relative low energy conformations of Ibrutinib and (R$_a$)-3.1 in the absence of BTK using Gaussian16 software. The calculations showed Ibrutinib's lowest energy conformation possessed the PP scaffold in an equatorial position off the (R)-piperidine in an exo conformation (away from chair) directing the piperidine's axial C—H's towards the PP scaffold's N-2 electron lone pair. In this pose, the acrylamide's β-carbon is extended out from the PP scaffold and 'into the page', mimicking the orientation Ibrutinib engages BTK's Cys481 in co-crystal structures. On the other hand, (R$_a$)-3.1 existed at a relative high energy conformation (+4.8 kcal/mol) when its (R)-piperidine is forced into the exo conformation due to a 1,3 diaxial strain between the C—H piperidine hydrogens and the C-2 methyl group. This interaction forces the PPY-piperidine bond to rotate 180° away from the methyl group to an endo conformation (0 kcal/mol). In this conformation the acrylamide β-carbon is pointed 'out of the page' aligning with conformation seen in the docking studies suggesting (R$_a$)-3.1's lowest energy conformation is unable to covalently interact with Cys481 resulting in substantial loss in affinity towards BTK compared to Ibrutinib (2.3 nM vs 3307 nM BTK IC$_{50}$). Because the C-2 methyl is necessary for stabilizing the atropisomeric axis, we hypothesized that if (R$_a$)-3.1's piperidine endo conformation was optimized to orientate acrylamide in the proper direction, we can regain a covalent interaction with BTK. To accomplish this, we synthesized (R$_a$)-3.2 possessing an (S)-piperidine, which places the piperidine nitrogen on the opposite side of the chair, demonstrating a 10× improvement in affinity towards BTK over its diastereomer (R$_a$)-3.1 (425 nM vs 3307 nM BTK IC$_{50}$).

While (R$_a$)-3.2's acrylamide was positioned in the general vicinity for covalent binding, molecular docking showed (R$_a$)-3.2 had to extend its endo-(S)-piperidine into a strained, unfavorable conformation to reach the Cys481 perhaps explaining the lowered BTK affinity compared to Ibrutinib (2.3 nM vs 425 nM BTK IC$_{50}$). To investigate this, we synthesized a series of controls beginning with 3.3 where we removed the aryl methyl group from 3.2 (Table 3). 3.3 showed no improvement of potency towards BTK (444 nM) suggesting the C-2 methyl and endo-(S)-piperidine combination was cause of decreased BTK affinity and not the rigid atropisomeric axis or aryl methyl group. Synthesizing and testing a pair of PPY controls without any ortho substituents (3.4 and 3.5) showed 1) there was no discernible difference between the PP and PPY scaffold (3.4's 2.7 nM vs Ibrutinib's 2.3 nM BTK $IC_{50}$) and 2) when unsubstituted at C-2, the PPY (R)-piperidine relaxes to the favorable exo conformation to bind BTK's Cys481, similar to Ibrutinib. With no ortho substitution, 3.4 and 3.5 possess the same conformational freedom about the atropisomeric axis as Ibrutinib and are likely equally as promiscuous. In attempts to tune low energy conformational window to increase selectivity, we incorporated a methyl group to aryl's ortho position in 3.6, and its PP analog 3.7. Again, there was minimal differences in BTK potency between the PPY scaffold (3.6) and PP scaffold (3.7) (6.4 nM vs 5.5 nM BTK $IC_{50}$) and each inhibitor maintained similar level of potency to the unsubstituted analog, 3.4 (2.7 nM BTK $IC_{50}$). While 3.6's BTK/BLK selectivity is about 2×, its CEP was narrowed by 40° potentially precluding it from binding other untested kinases (FIG. 1B).

To try and further narrow 3.6/3.7's CEP, we synthesized and tested a 2,6-dimethyl aryl analog (3.8) (FIG. 1B) which lost affinity to BTK compared to 3.7 (5.5 nM vs 37.4 nM), perhaps in part, due to overcorrecting 3.8's CEP towards orthogonality (−90°) making it unable to adopt the binding conformation preferred by BTK at −120°. In efforts to re-correct 3.8's CEP, we calculated the CEP for a PPY with a 2-fluoro,6-methyl aryl (3.9) and found it possessed limited low energy conformational window tuned to BTK's binding range.

TABLE 3

Kinase inhibition data for compounds 3.3-3.8

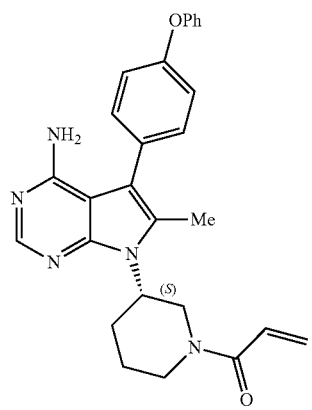

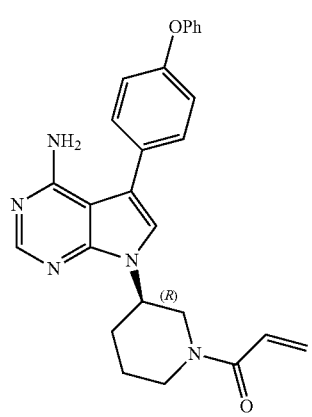

TABLE 3-continued

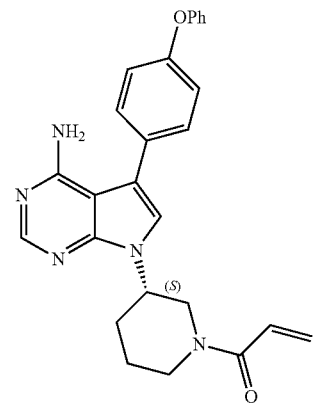

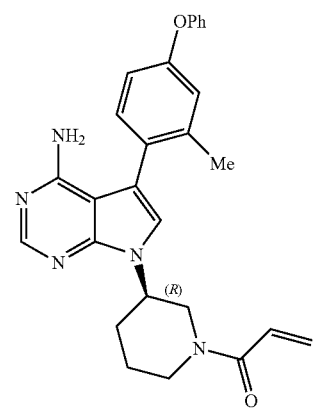

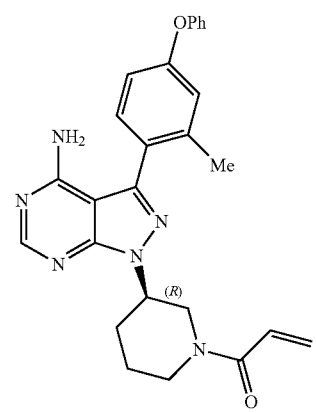

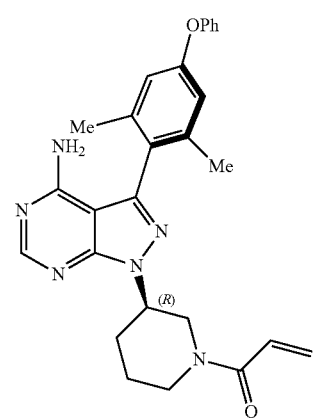

TABLE 3-continued

| Kinase IC$_{50}$ (nM) | 3.3 | 3.4 | 3.5 | 3.6 | 3.7 | 3.8 |
|---|---|---|---|---|---|---|
| BTK | 444 | 2.7 | 17.3 | 6.4 | 5.5 | 37.4 |
| BLK | 451 | 9.1 | 55.9 | 14.0 | 8.4 | 174 |

The PP scaffold was chosen for 3.8 and 3.9 because of low yields when cross-coupling the iodinated PPY scaffold to sterically hindered 2,6-disubstituted boronic esters. The synthesis of the PP scaffold provided an alternate route where the heterocycle-aryl C—C bond is instead formed through an aryl Grignard addition prior to cyclizing the PP scaffold (Scheme 2). The precursor to the aryl Grignard was formed by subjecting the brominated phenol to a Chan Lam coupling with phenyl boronic acid yielding a brominated diaryl ether. This substrate was then was reacted with activated Mg° and added into 4,6-dichloropyrimidine-5-carbaldehyde under inert atmosphere to afford an alcohol intermediate. Following oxidation with Dess-Martin periodinane, the ketone substrate was reacted with hydrazine monohydrate to effectively cyclize the pyrazolo portion of the PP scaffold. The PP scaffold was subjected to a Mitsunobu reaction with the (S)-N-boc-protected 3-hydroxypiperidine. Subsequent steps of amination (protected), deprotection and addition of acryloyl chloride were followed according to the previous PPY synthetic route (Scheme 1).

Scheme 2. Synthesis of pyrazolopyrimidine compounds 3.7-3.9.

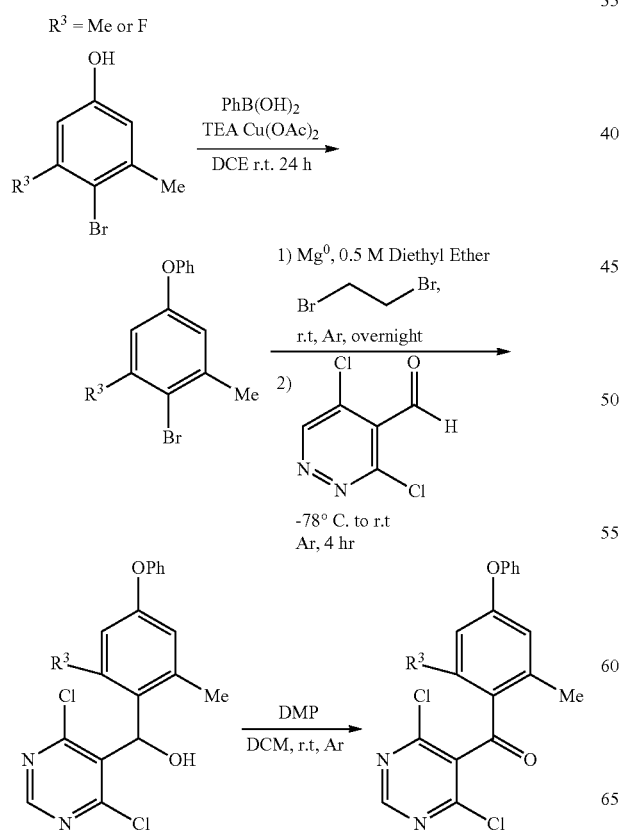

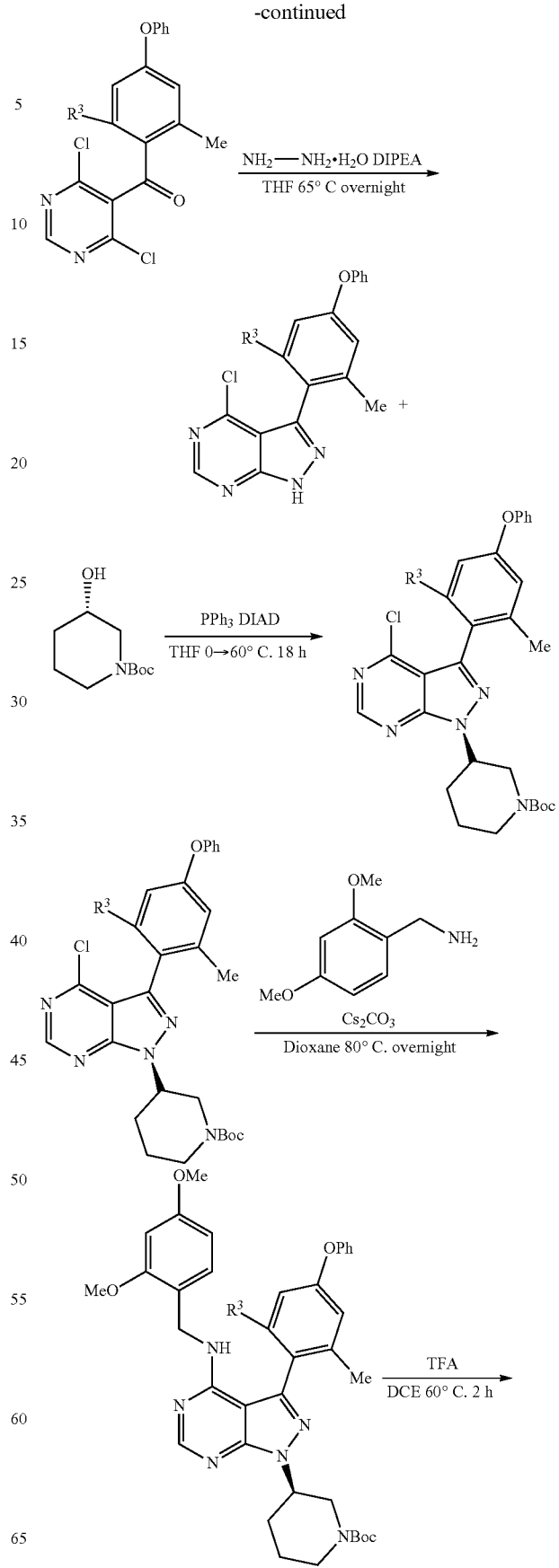

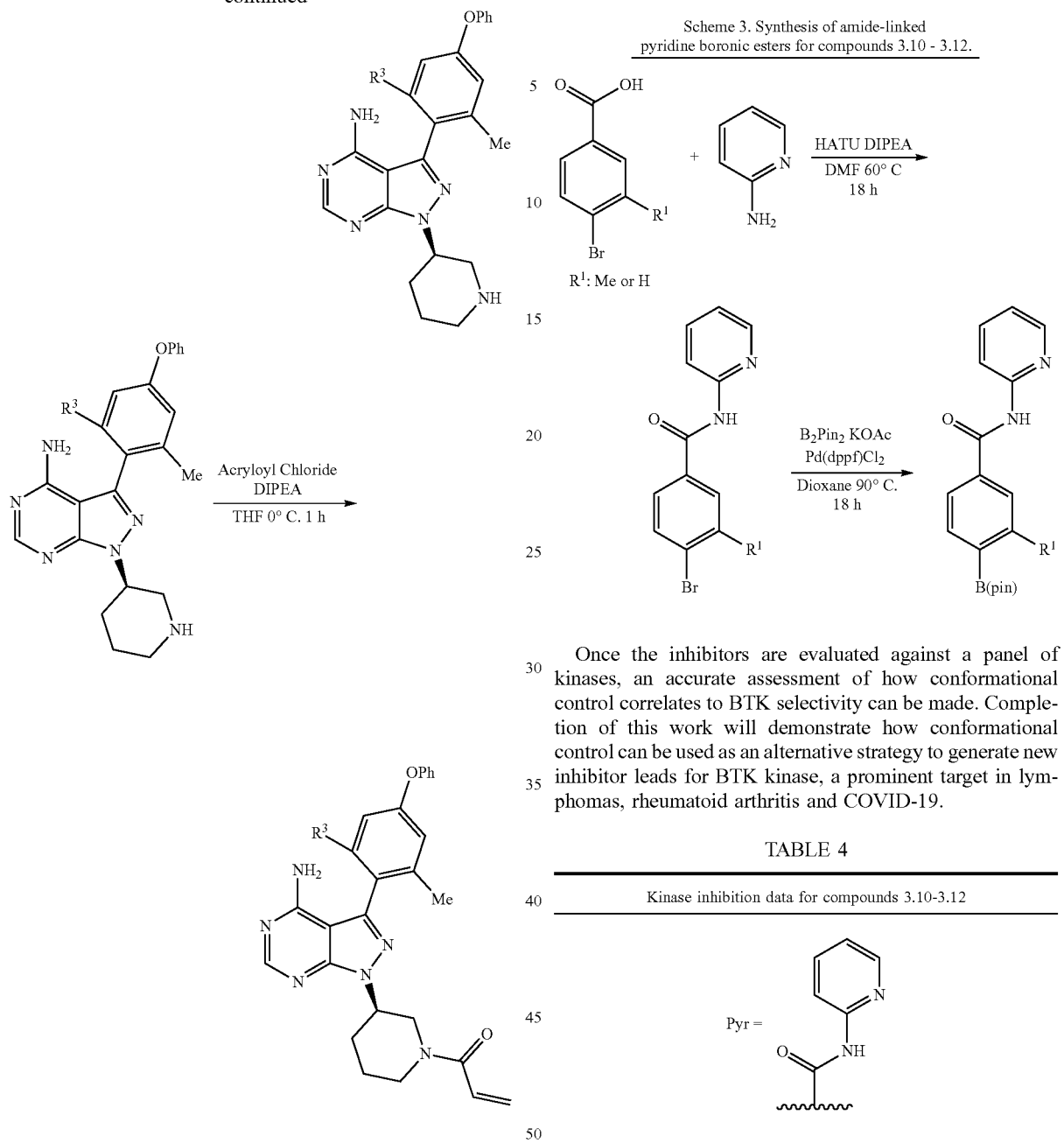

Scheme 3. Synthesis of amide-linked pyridine boronic esters for compounds 3.10 - 3.12.

Once the inhibitors are evaluated against a panel of kinases, an accurate assessment of how conformational control correlates to BTK selectivity can be made. Completion of this work will demonstrate how conformational control can be used as an alternative strategy to generate new inhibitor leads for BTK kinase, a prominent target in lymphomas, rheumatoid arthritis and COVID-19.

TABLE 4

Kinase inhibition data for compounds 3.10-3.12

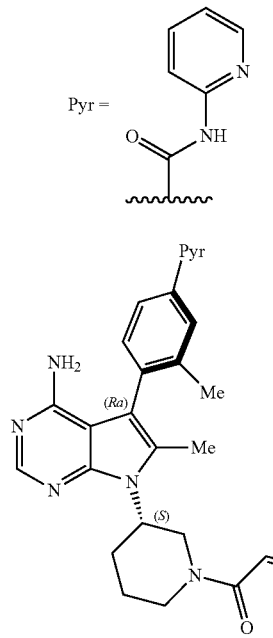

We next sought to optimize the inhibitor's aryl ether extension towards the interior of BTK's binding pocket. Guided by Acalabrutinib's potent gate-keeper aryl, we synthesized a set of atropisomeric analogs, $(R_a)$-3.10 and $(S_a)$-3.10, that possessed an optimized amide-linked pyridine at the aryl's para position (Scheme 3) along with (S)-piperidine enantiomer and C-2 and aryl methyl groups. $(R_a)$-3.10 proved to be quite potent towards BTK compared to its aryl ether equivalent, $(R_a)$-3.2, (24.2 nM vs 425 nM BTK $IC_{50}$, Table 4). Following the trends from the aryl ether set of compounds, we synthesized and tested an optimized analog with an (R)-piperidine and no C-2 substituent (3.11) arriving at our most promising inhibitor yet with a 1.12 nM $IC_{50}$ affinity towards BTK and 30× selectivity over BLK. To understand the extent that 3.11's narrowed CEP increased selectivity, we synthesized an unsubstituted analog 3.12.

TABLE 4-continued

[Chemical structure: 4-amino pyrrolopyrimidine with Pyr and Me substituents on phenyl, Me on pyrrole, and (S)-acryloyl piperidine — labeled (Sa), (S)]

[Chemical structure: 4-amino pyrazolopyrimidine with Pyr and Me substituents on phenyl and (R)-acryloyl piperidine — labeled (R)]

[Chemical structure: 4-amino pyrazolopyrimidine with Pyr on phenyl and (R)-acryloyl piperidine — labeled (R)]

| Kinase IC$_{50}$ (nM) | (Ra)-3.10 | (Sa)-3.10 | 3.11 | 3.12 |
|---|---|---|---|---|
| BTK | 24.2 | 21.7 | 1.12 | — |
| BLK | 128 | 90.4 | 32.4 | — |

Example 2. Pharmaceutical Dosage Forms

The following formulations illustrate representative pharmaceutical dosage forms that may be used for the therapeutic administration of a compound (e.g., an atropisomer) of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Areosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An atropisomer compound of Formula I:

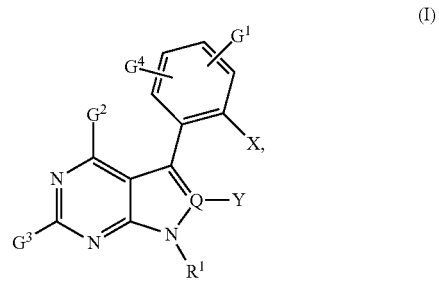

or salt thereof;
wherein
$G^1$ is aryloxy, halo, hydroxy, alkyl, alkoxy, amino, amido, or phenyl;
$G^2$ is amino, halo, hydroxy, alkyl, alkoxy, arylnoxy, amido, or phenyl;
$G^3$ and $G^4$ are independently H, halo, hydroxy, alkyl, alkoxy, or amino;
Q is C or N;
X and Y taken together form an atropisomerism rotational blocking moiety; and
$R^1$ is a buttressing substituent wherein the buttressing substituent comprises a ring heteroatom and an electrophile;
wherein the atropisomer is atropisomerically stable; and
wherein the selectivity of the atropisomer is modulated compared to a corresponding rapidly interconverting parent kinase inhibitor, wherein the atropisomerism rotational blocking moiety of the atropisomer in combination with the buttressing substituent produces a barrier to rotation of at least 10 kcal/mol, and the atropisomeric purity of the atropisomer has a half-life of at least 8 hours, thereby stabilizing atropisomerism of the atropisomer having modulated kinase selectivity.

2. The compound of claim 1 wherein $R^1$ is a nitrogen heterocycle wherein the nitrogen heterocycle is substituted with a Michael acceptor.

3. The compound of claim 2 wherein $R^1$ is:

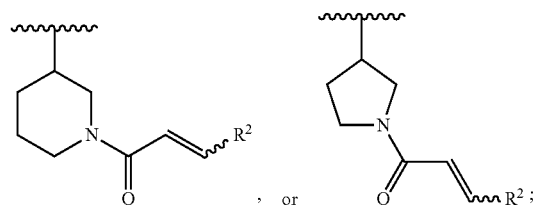

wherein $R^2$ is H, halo, nitro, or —$(C_1$-$C_6)$alkyl.

4. The compound of claim 1 wherein X is —$(C_1$-$C_6)$alkyl, halo, hydroxy, —O$(C_1$-$C_6)$alkyl, or amino.

5. The compound of claim 1 wherein Q is C and Y is —$(C_1$-$C_6)$alkyl, halo, hydroxy, —O$(C_1$-$C_6)$alkyl, or amino, wherein —$(C_1$-$C_6)$alkyl is optionally substituted;
or Q is N and Y is lone pair.

6. The compound of claim 1 wherein $G^1$ is OPh, or —(C═O)NR$^a$heteroaryl wherein R$^a$ is H or —$(C_1$-$C_6)$alkyl.

7. The compound of claim 1 wherein $G^2$ is $NH_2$.

8. The compound of claim 1 wherein $G^3$ is H and $G^4$ is H, F, or $CH_3$.

9. The compound of claim 1 wherein the compound is an atropisomer having an $(R_a)$-configuration in reference to the bond joining the phenyl moiety to the 5-membered heterocyclic ring of Formula I.

10. The compound of claim 1 wherein the compound is an atropisomer having an $(S_a)$-configuration in reference to the bond joining the phenyl moiety to the 5-membered heterocyclic ring of Formula I.

11. The compound of claim 1 wherein the compound of Formula I is a compound of Formula II, Formula IIB, or Formula V:

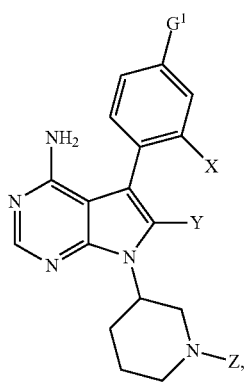
(II)

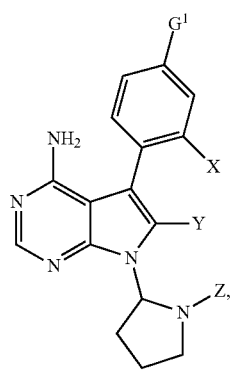
(IIB)

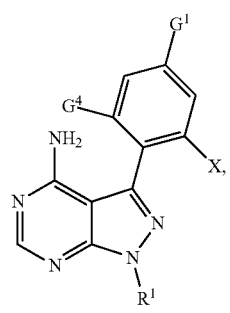
(V)

or salt thereof;

wherein
G¹ is aryloxy or amido;
G⁴ is H, halo, hydroxy, alkyl, alkoxy, or amino;
R¹ is:

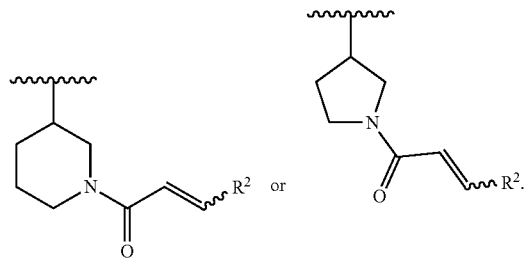

wherein R² is H, halo, nitro, or —$(C_1-C_6)$alkyl;
X is halo alkyl, alkoxy, or amino;
Y is halo alkyl, alkoxy, or amino; and
Z is acyl.

12. The compound of claim 11 wherein X and Y are $CH_3$.

13. The compound of claim 11 wherein G¹ is OPh or —(C=O)NHpyridyl.

14. The compound of claim 11 wherein Z is:

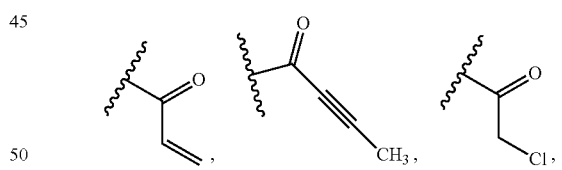

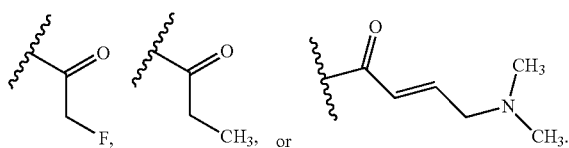

15. The compound of claim 11 wherein the compound is:

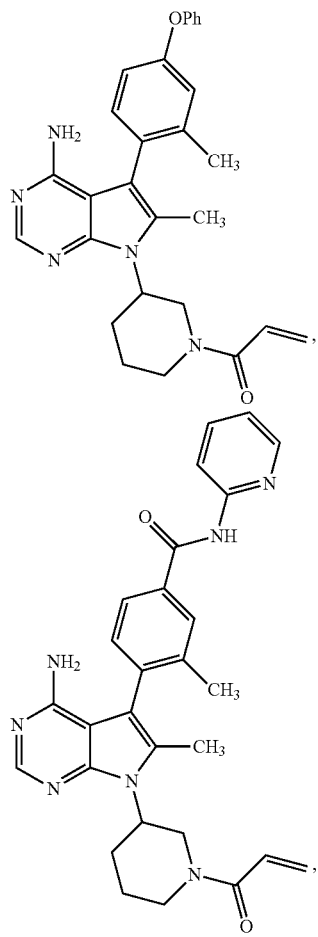

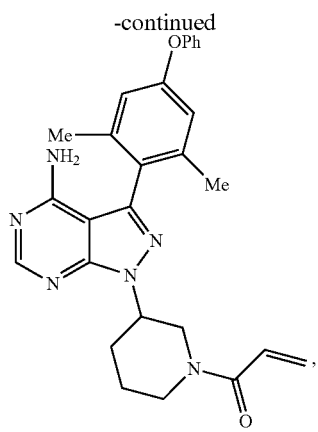

or salt thereof.

16. A pharmaceutical composition comprising the compound of claim 1 in combination with a pharmaceutically acceptable diluent, carrier, or excipient.

17. A method for the treatment of blood cancer in a subject in need thereof comprising administering an effective amount of an atropisomer of claim 1, thereby treating the cancer.

18. The method of claim 17 wherein the atropisomer is selective for BTK kinase over other kinases.

* * * * *